US011883638B2

(12) United States Patent
Sealfon et al.

(10) Patent No.: US 11,883,638 B2
(45) Date of Patent: *Jan. 30, 2024

(54) NEEDLE INSERTION DEVICE

(71) Applicant: REPRO-MED SYSTEMS, INC., Chester, NY (US)

(72) Inventors: Andrew I Sealfon, Monroe, NY (US); Christopher Erol Ogut, Vernon, NJ (US)

(73) Assignee: KORU Medical Systems, Inc., Mahwah, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 18/071,775

(22) Filed: Nov. 30, 2022

(65) Prior Publication Data

US 2023/0166053 A1 Jun. 1, 2023

Related U.S. Application Data

(60) Continuation of application No. 16/551,481, filed on Aug. 26, 2019, now Pat. No. 11,559,635, which is a
(Continued)

(51) Int. Cl.
*A61M 5/42* (2006.01)
*A61M 25/06* (2006.01)

(52) U.S. Cl.
CPC .............. *A61M 5/422* (2013.01); *A61M 5/42* (2013.01); *A61M 5/425* (2013.01); *A61M 5/427* (2013.01); *A61M 25/0637* (2013.01)

(58) Field of Classification Search
CPC ........ A61M 5/42; A61M 5/422; A61M 5/425; A61M 5/427; A61M 25/0637;
(Continued)

(56) References Cited

U.S. PATENT DOCUMENTS 10,478,569 B2 * 11/2019 Sealfon .................. A61M 5/427
11,559,635 B2 * 1/2023 Sealfon .................... A61M 5/42
(Continued)

FOREIGN PATENT DOCUMENTS

DE 10 2004 025651 12/2005
WO WO 99/33504 7/1999

OTHER PUBLICATIONS

Extended European Search Report for Application 14783133.3-1664 / 2983744 PCT/US2014033060 dated Mar. 1, 2017 (Mar. 1, 2017).

*Primary Examiner* — Nathan R Price
*Assistant Examiner* — Anh Bui
(74) *Attorney, Agent, or Firm* — Daniel W. Roberts; Law Offices of Daniel W. Roberts, LLC

(57) ABSTRACT

The present invention generally provides a device for inserting needles and alleviating the discomfort associated with needle insertion. In certain embodiments, the device is suited for injecting butterfly needles and particularly butterfly needles that are attached to infusion tubing. The patient or caregiver loads a butterfly needle with tubing attached into the base of the drive plunger. The needle with tubing attached is retracted into the housing of the device by retracting the inner plunger. Once retracted, the device is activated and ready to administer a needle into the tissue of a patient. The device is then placed on the location of the skin where injection is desired. The surface that contacts the skin may be textured and may include a contact switch that causes the device to vibrate when slight pressure is applied through contact with the skin. Two trigger buttons in the housing of the device may be depressed to eject the needle at an angle essentially perpendicular to the surface of the skin into the tissue of the patient concurrently with the textured pads contacting the skin and vibrating, distracting the patient from the needle insertion. The inner plunger of
(Continued)

the device is then depressed toward the surface of the skin to release the needle from the device. The wings and body of the butterfly may be secured to the skin, for example, with an adhesive such as tape.

19 Claims, 18 Drawing Sheets

Related U.S. Application Data division of application No. 14/783,076, filed as application No. PCT/US2014/033060 on Apr. 4, 2014, now Pat. No. 10,478,569.

(60) Provisional application No. 61/972,254, filed on Mar. 29, 2014, provisional application No. 61/809,391, filed on Apr. 7, 2013.

(58) Field of Classification Search
CPC .......... A61M 25/0102; A61M 25/0606; A61M 2005/1585
See application file for complete search history.

(56) References Cited

U.S. PATENT DOCUMENTS

| | | |
|---|---|---|
| 2005/0131346 A1 | 6/2005 | Douglas |
| 2009/0216215 A1* | 8/2009 | Thalmann ......... A61M 25/0612 604/506 |
| 2012/0245497 A1* | 9/2012 | Nicholls ................ A61H 7/005 601/136 |
| 2014/0074062 A1* | 3/2014 | Caffey ................ A61M 5/1452 604/82 |

* cited by examiner

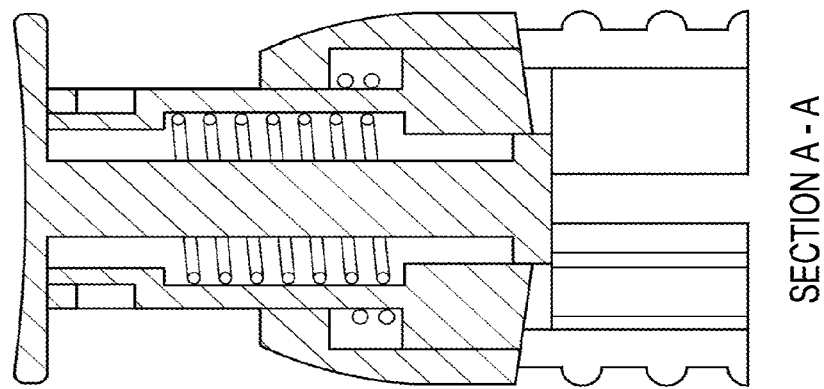
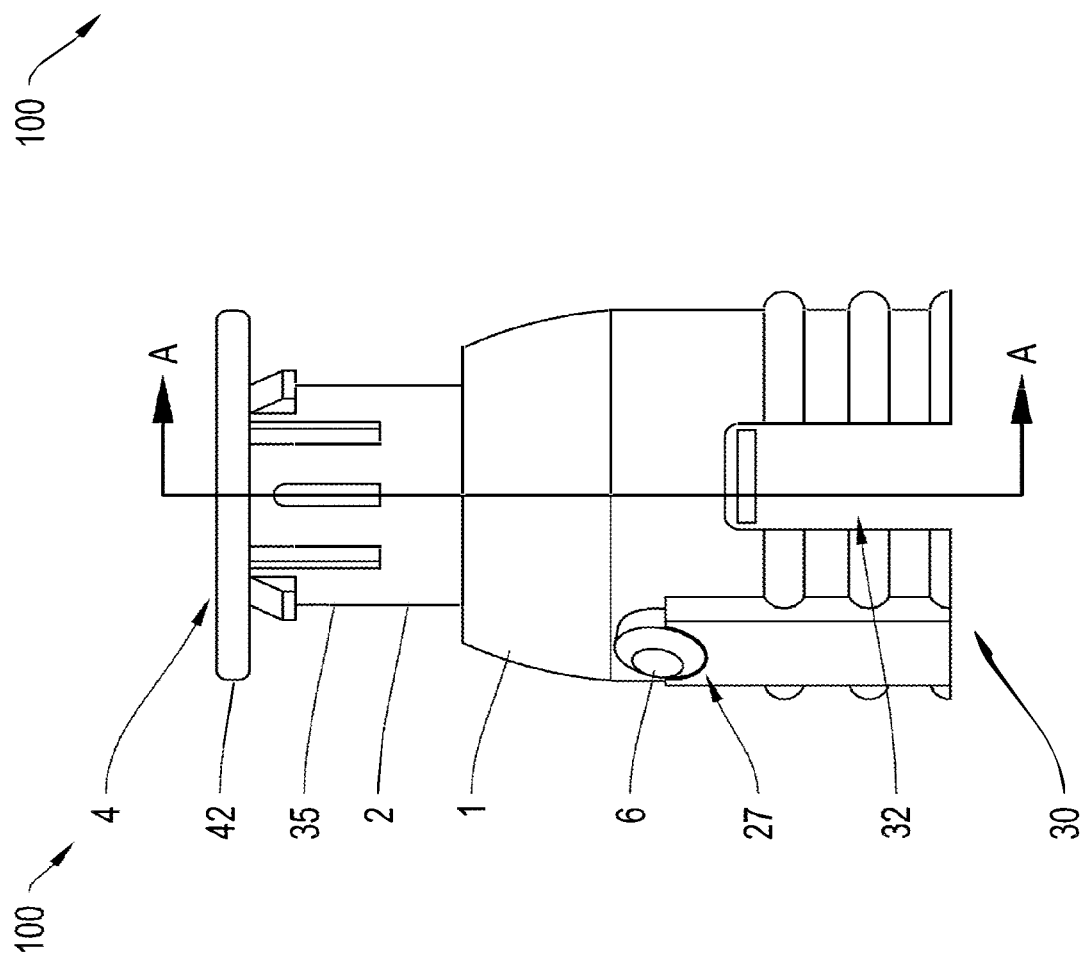

SECTION B - B

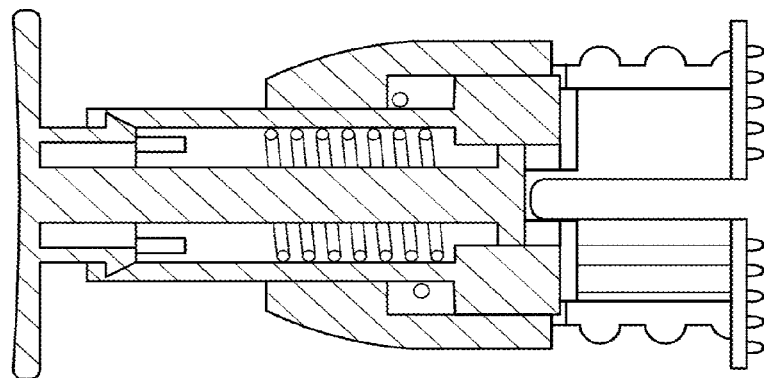
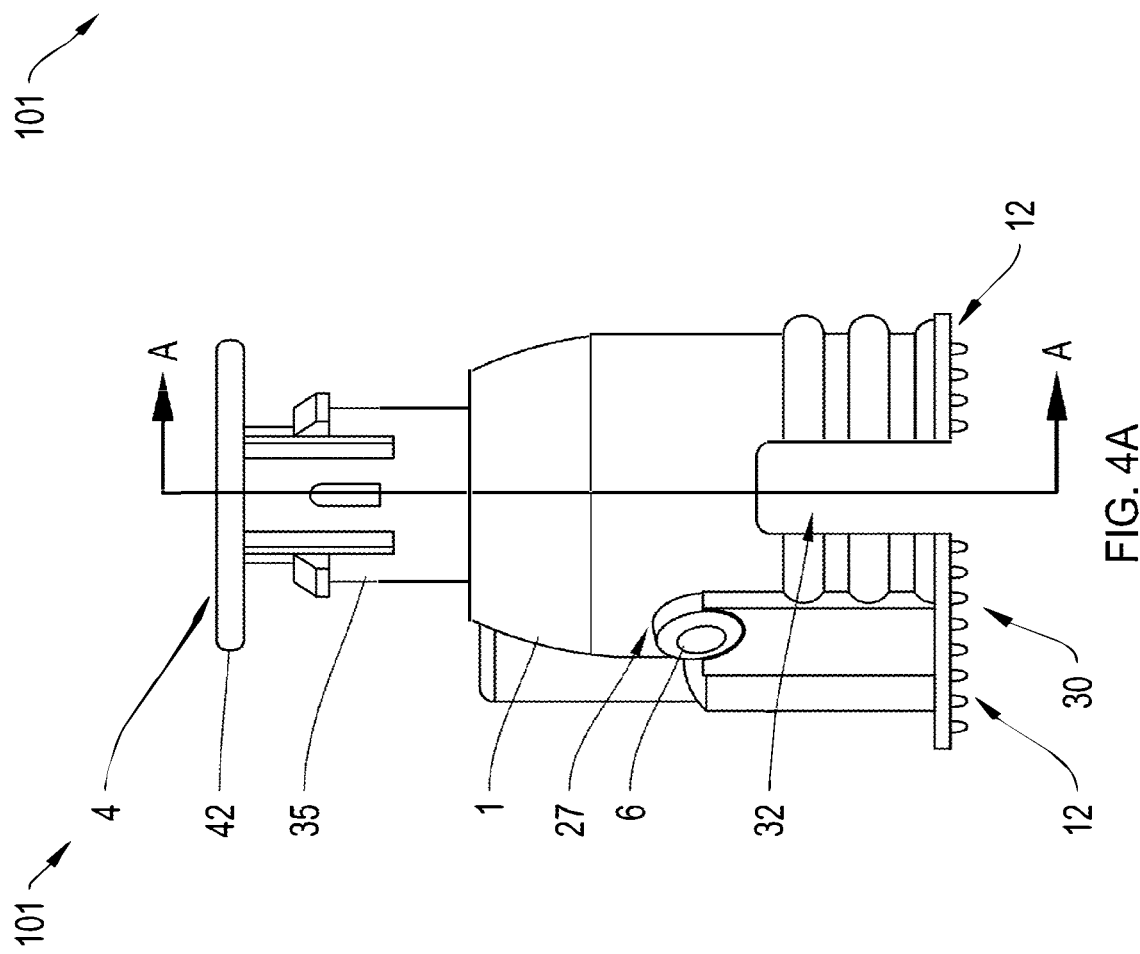
FIG. 4A
SECTION A - A
FIG. 4B

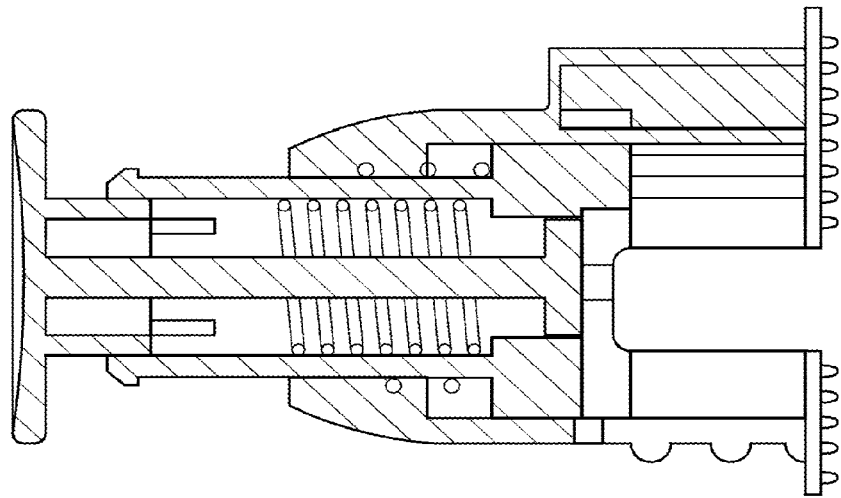
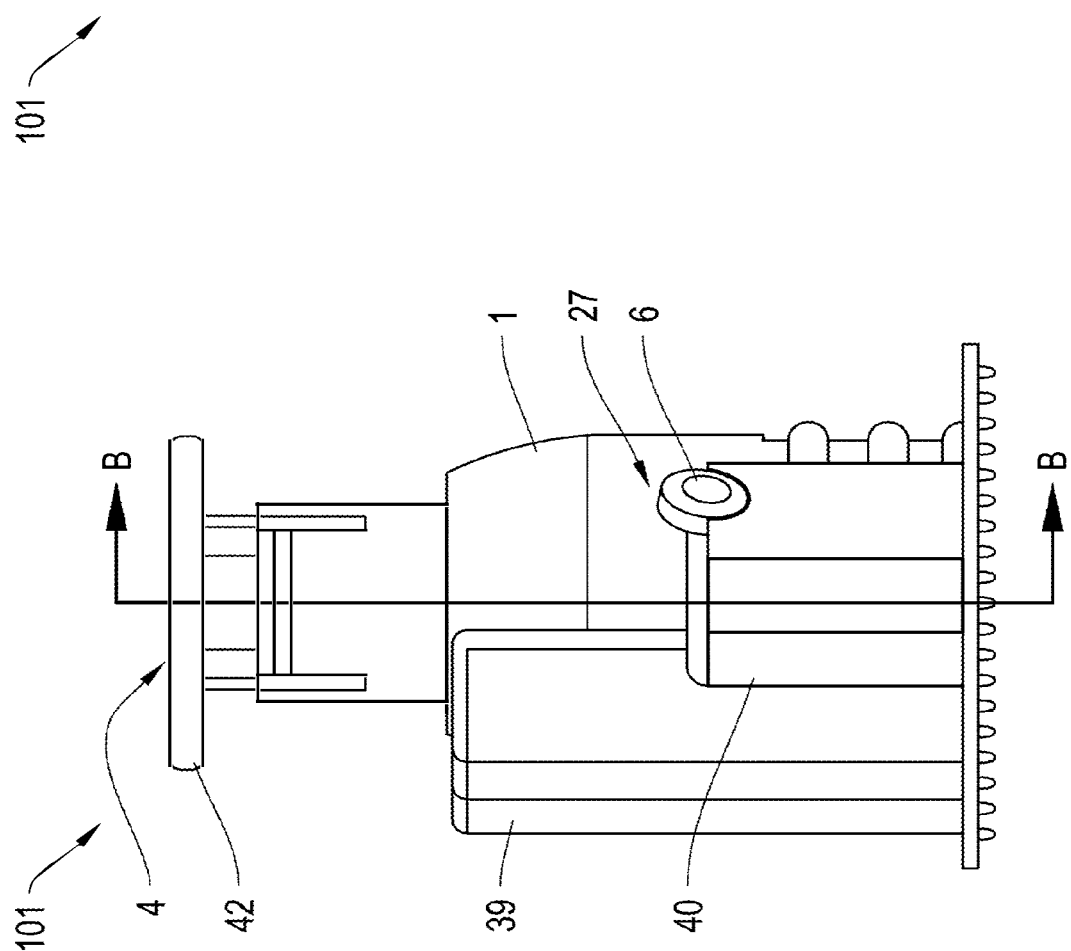

NEEDLE INSERTION DEVICE

CROSS REFERENCE TO RELATED APPLICATIONS

The present application is continuation of U.S. patent application Ser. No. 16/551,481 filed on Aug. 26, 2019, now U.S. patent Ser. No. 11/559,639, which was a Divisional of U.S. application Ser. No. 14/783,076, filed Oct. 7, 2015, now U.S. Pat. No. 10,478,569 issued on Nov. 19, 2019. This continuation application claims the benefit of U.S. patent application Ser. No. 14/783,076, filed Oct. 7, 2015, incorporated by reference, which is a National Stage of International Application PCT/US2014/033060, filed Apr. 7, 2014 which claims the benefit under 35 U.S.C. § 119(e) to U.S. provisional application Nos. 61/809,391, filed Apr. 7, 2013, and 61/972,254, filed Mar. 29, 2014 the contents of each of which are incorporated herein by reference in their entirety.

FIELD OF THE INVENTION

The subject matter disclosed herein relates to devices for inserting needles into tissue and methods of use.

BACKGROUND OF THE INVENTION

Certain therapies such as immune globulin therapy can be self-administered by a patient or by a caregiver to a patient in the comfort of the patient's home. Infusion therapies require the user or caregiver to insert one or more needles into the patient's body. While some patients have no difficulty self-inserting needles or receiving needles in their body, other patients are sensitive to the pain of the injection or are uncomfortable seeing needles or injecting needles into their body. In particular, many children have difficulty receiving infusion therapy due to the pain of needle insertion or fear of needles.

The method in which the needle is injected into the tissue is relevant to preventing pain. Research has shown that the speed of the insertion of the needle is important to protect the tissue layers from rupturing and reduce the pain of the insertion. When a needle is slowly inserted into the tissue, more rupture events are observed in the tissue as compared to the rapid insertion of a needle into tissue.

Topical anesthesia is one way to help alleviate the pain at the site of the insertion. Topical creams may be applied in advance of the insertion of a needle to help numb the skin. These creams may take some time to take effect and some people are sensitive to components in the creams. Other methods for topical anesthesia include contacting the skin with low temperatures to numb the area or using vibrations on the surface of the skin near the injection site.

Many of the therapies that require infusions are given on a weekly or biweekly basis and some even more frequently. In order to streamline the infusion process, it would be helpful to have a device that overcomes many of the difficulties associated with injecting needles into the body such as alleviating pain, and alleviating patient fears. There remains a need for a device for injecting needles into patients who are sensitive to the pain of the injection or are uncomfortable seeing needles or injecting needles into their body.

SUMMARY OF THE INVENTION

A device for administering a needle to a subject, comprising: a housing comprising a shell with a distal opening and a proximal opening; a drive plunger occupying the space defined by the shell of the housing and in shifting engagement with the housing, wherein the drive plunger has a proximal end with a handle extending from the proximal opening of the housing and a distal end dimensioned to receive and deliver a needle; a drive spring associated with the drive plunger such that when the handle is retracted proximally relative to the housing, the drive spring compresses and when the drive plunger is released, the drive plunger travels distally from the force of the drive spring; and a component for relieving discomfort associated with injecting a needle to the subject receiving the injection.

The component for relieving the discomfort to the patient is selected from one or more of a textured pad on the distal surface of the housing and a vibrator component. The device may comprise both a textured pad on the distal surface of the housing and a vibrator component.

The device may comprise a stop to hold the drive spring in a retracted position. The stop may be one or more buttons extending from the surface of the drive plunger. Depression of the button may release the drive plunger from its retracted state. In certain embodiments, when the drive plunger is released, the needle is injected into the skin of the subject. When the needle is injected into the skin of the subject, the distal end of the drive plunger may release the needle from the device.

The distal surface of the drive plunger may be dimensioned to receive a butterfly needle. In certain embodiments, the needle is attached to infusion tubing. In certain embodiments, the device further comprises a needle positioned in the distal surface of the drive plunger such as a butterfly needle.

A device for administering a butterfly needle to a subject, comprising: a housing comprising a shell with a distal opening and a proximal opening; a drive plunger occupying the space defined by the shell of the housing and in shifting engagement with the housing, wherein the drive plunger has a proximal end with a handle extending from the proximal opening of the housing and a distal end dimensioned to receive and deliver a butterfly needle; and a drive spring associated with the drive plunger such that when the handle is retracted proximally relative to the housing, the drive spring compresses and when the drive plunger is released, the drive plunger travels distally from the force of the drive spring. In certain embodiments, the device further comprises a component for relieving discomfort associated with injecting a needle to the subject receiving the injection.

A device for relieving the pain or discomfort of a subject associated with receiving administration of a needle, comprising: a housing with a proximal and distal end wherein the distal end has a distal surface for contacting skin; one or more textured pads positioned on the distal surface of the housing for contacting the surface of the skin; a vibrator motor and power source associated with the housing such that the power source supplies power to the vibrator motor when the motor is activated; a contact switch on the distal surface of the housing which activates the vibrator motor and causes the device to vibrate upon contact with skin.

FIGURES OF THE INVENTION

FIG. 1 (A) is a first side view of a needle insertion device 100 according to certain embodiments, FIG. 1(B) is a cross-sectional view A-A of a needle insertion device 100 according to certain embodiments, FIG. 1(C) is a top view of a needle insertion device 100 according to certain embodiments, FIG. 1(D) is a bottom view of a needle insertion device 100 according to certain embodiments;

FIG. 2 (A) is a second side view of a needle insertion device 100 according to certain embodiments, FIG. 2(B) is a cross-sectional view B-B of a needle insertion device 100 according to certain embodiments, FIG. 2 (C) is a perspective assembled view of a insertion device 100 according to certain embodiments;

FIG. 3 is a perspective, exploded view of a needle insertion device 100 according to certain embodiments of the present disclosure, and includes an assembly having a housing 1, a drive plunger 2 associated with a drive spring 3 and an inner plunger 4 wherein the drive spring 3 provides the force for advancing the drive plunger 2 and needle into the skin of a subject;

FIG. 4 (A) is a first side view of a needle insertion device 101 according to certain embodiments, FIG. 4(B) is a cross-sectional view A-A of a needle insertion device 101 according to certain embodiments, FIG. 4(C) is a top view of a needle insertion device 101 according to certain embodiments, FIG. 4(D) is a bottom view of a needle insertion device 101 according to certain embodiments;

FIG. 5 (A) is a second side view of a needle insertion device 101 according to certain embodiments, FIG. 5(B) is a cross-sectional view B-B of a needle insertion device 101 according to certain embodiments, FIG. 5 (C) is a perspective assembled view of a insertion device 101 according to certain embodiments;

FIG. 6 is a perspective, exploded view of a needle insertion device 101 according to certain embodiments of the present disclosure, and further includes textured pads 12, a vibrator motor 10 and power source 11;

FIG. 7 is a perspective, exploded view of a needle insertion device 102 according to certain embodiments of the present disclosure, and further includes a contact switch 14 associated with a contact spring 15 which activates a vibrator motor 10 upon compression of the contact switch 14;

FIG. 8 is a bottom view of device 102 with the drive plunger 2 in a non-retracted state;

FIG. 9 is a perspective view of the bottom of needle insertion device 102 with a butterfly needle with attached infusion tubing loaded into recessions 16 and 17 in the distal surface of the drive plunger 31 with the drive plunger 2 in a non-retracted state;

FIG. 10 is a bottom view of device 102 with a butterfly needle with attached infusion tubing loaded into recessions 16 and 17 in the distal surface of the drive plunger 31 with the drive plunger 2 in a non-retracted state;

Figure 13:
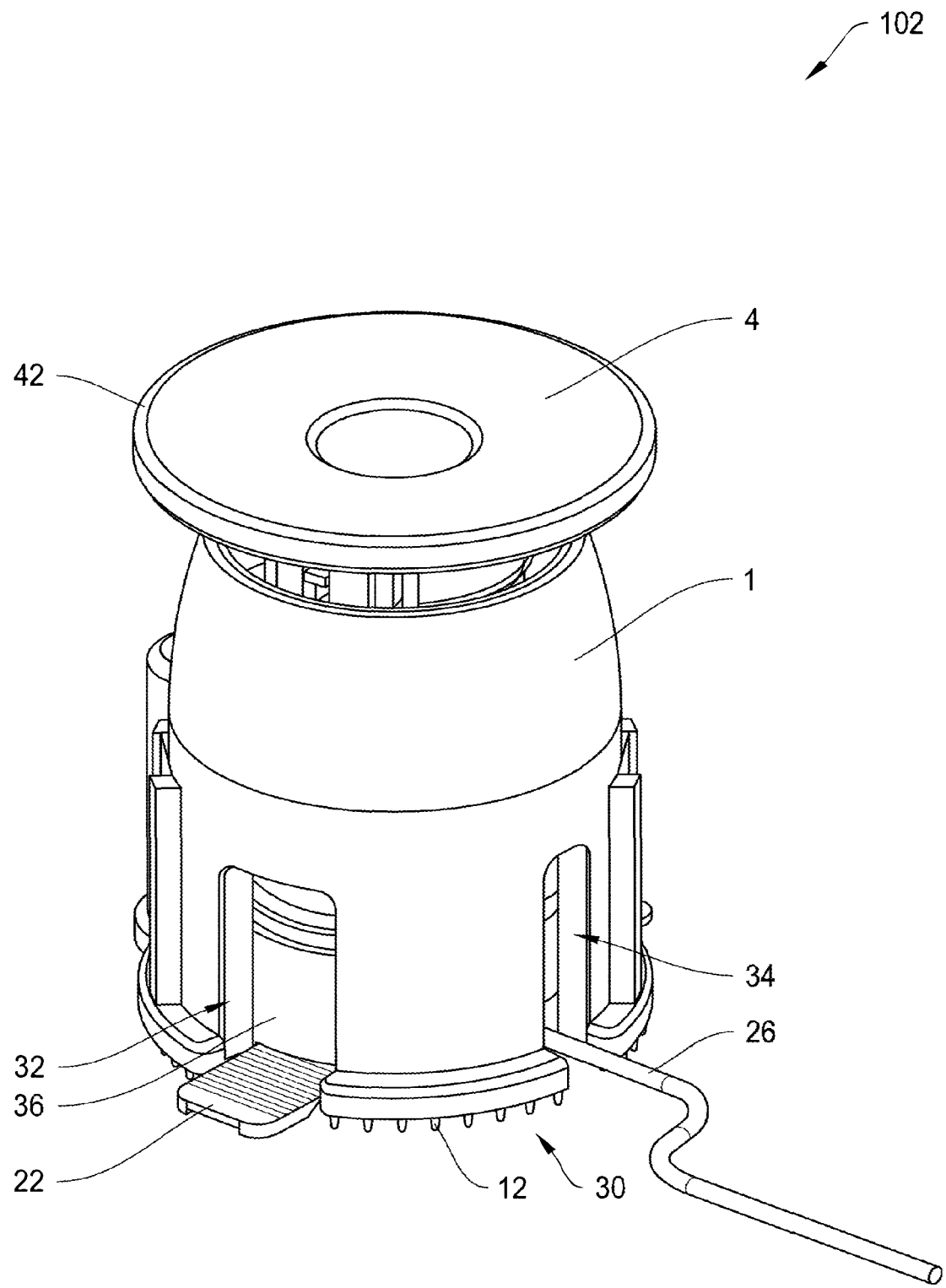
Figure 14:
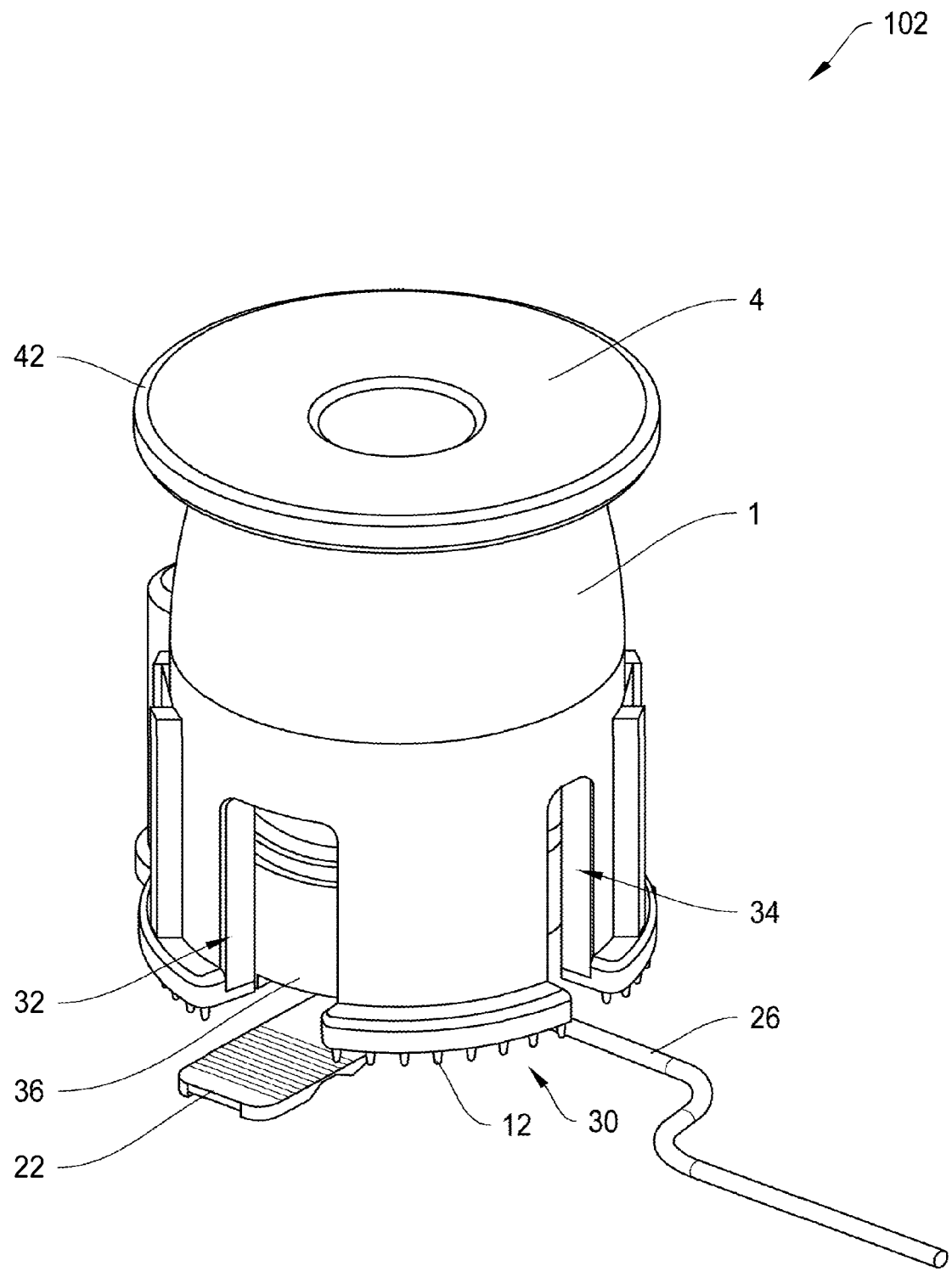

FIG. 13 is a perspective side view of the needle insertion device 102 loaded with a butterfly needle with the drive plunger 2 in a non-retracted state; and FIG. 14 is a perspective side view of the needle insertion device 102 with the inner plunger depressed to eject the butterfly needle from the device 102;

DETAILED DESCRIPTION OF THE INVENTION

Certain exemplary embodiments will now be described to provide an overall understanding of the principles of the structure, function, manufacture and use of the devices and methods disclosed herein. One or more examples of these embodiments are illustrated in the accompanying figures. Those of ordinary skill in the art will understand that the devices and methods specifically described herein and illustrated in the accompanying drawings are non-limiting exemplary embodiments. The features illustrated or described in connection with one exemplary embodiment may be combined with the features of other embodiments. For example, any features described in any one of devices 100, 101 and 102 may be combined with any features of the other devices. Such modifications and variations are intended to be included within the scope of the present invention.

The present invention generally provides a device for inserting needles and alleviating the discomfort associated with needle insertion. In certain embodiments, the device is suited for injecting butterfly needles and particularly butterfly needles that are attached to infusion tubing. The patient or caregiver loads a butterfly needle with tubing attached into the base of the drive plunger. The needle with tubing attached is retracted into the housing of the device by retracting the inner plunger. Once retracted, the device is activated and ready to administer a needle into the tissue of a patient. The device is then placed on the location of the skin where injection is desired. The surface that contacts the skin may be textured and may include a contact switch that causes the device to vibrate when slight pressure is applied through contact with the skin. The vibration and or textured pad may contact the skin for a period of time suitable to anesthetize the area. Two trigger buttons in the housing of the device may be depressed to eject the needle at an angle essentially perpendicular to the surface of the skin into the tissue of the patient concurrently with the textured pads contacting the skin and vibrating, distracting the patient from the needle insertion. The inner plunger of the device is then depressed toward the surface of the skin to release the needle from the device. The wings and body of the butterfly may be secured to the skin, for example, with an adhesive such as tape.

As used herein, the terms "subject" or "patient" mean the person receiving the needle injection. In some cases the subject is also a patient receiving a therapy. In other scenarios the subject may not be a patient such as a subject receiving a tattoo or other injection unrelated to treatment or prevention of a condition.

A "user" of the device means the person who is actively manipulating the device. The user may be the subject or patient or the user may be a third party such as a physician or a caregiver.

The "needle" or "needles" described herein refer to any kind of needle such as a disk needle, a butterfly needle, a needle associated with a cannula, a trocar with a catheter or any other needle injected into the skin.

Figure 1D:
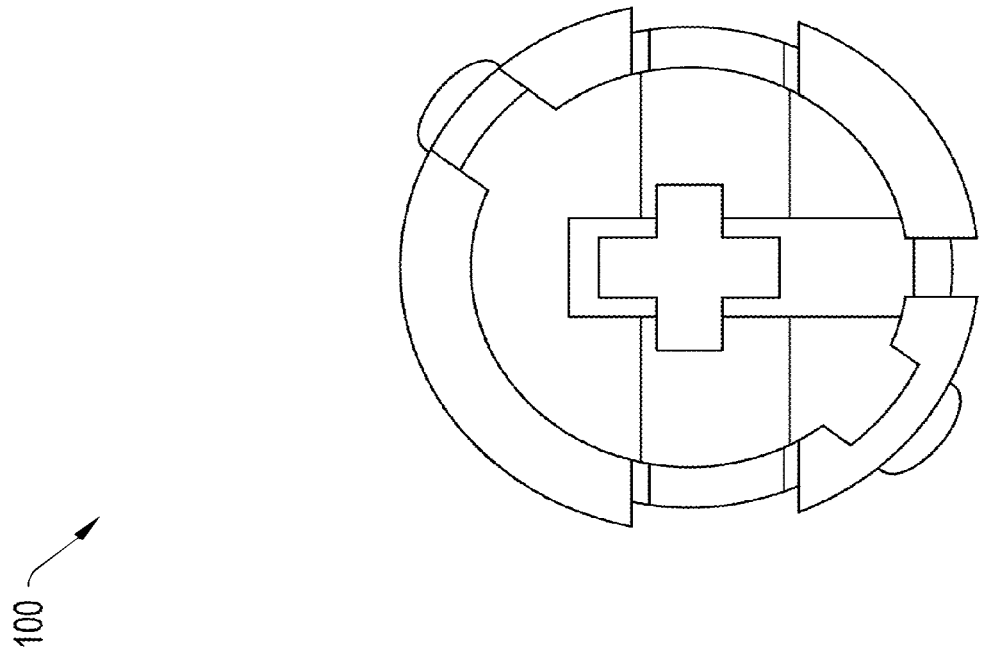
Figure 1C:
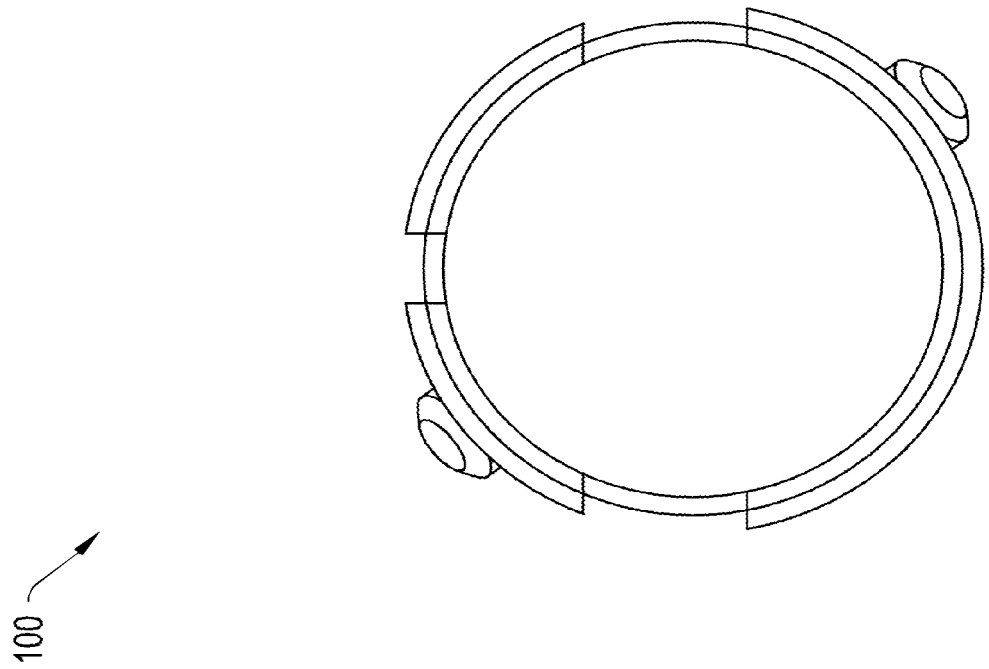
Figure 2B:
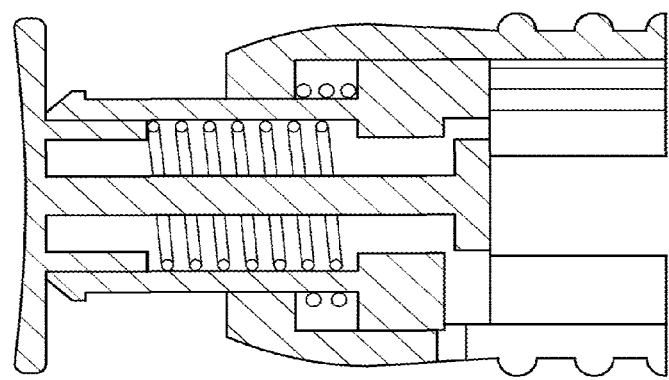
Figure 2A:
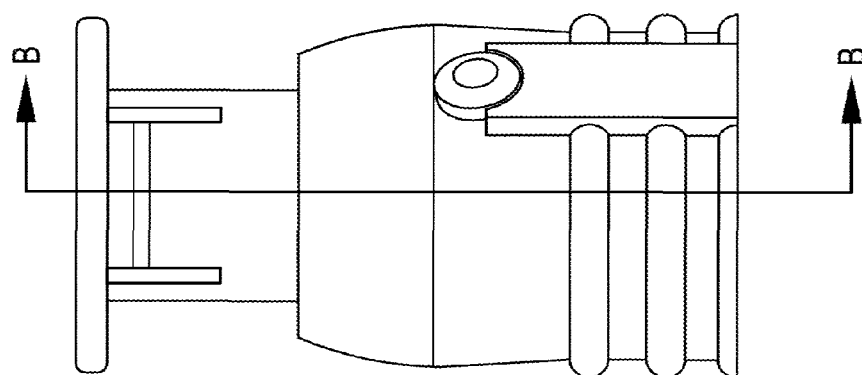
Figure 2C:
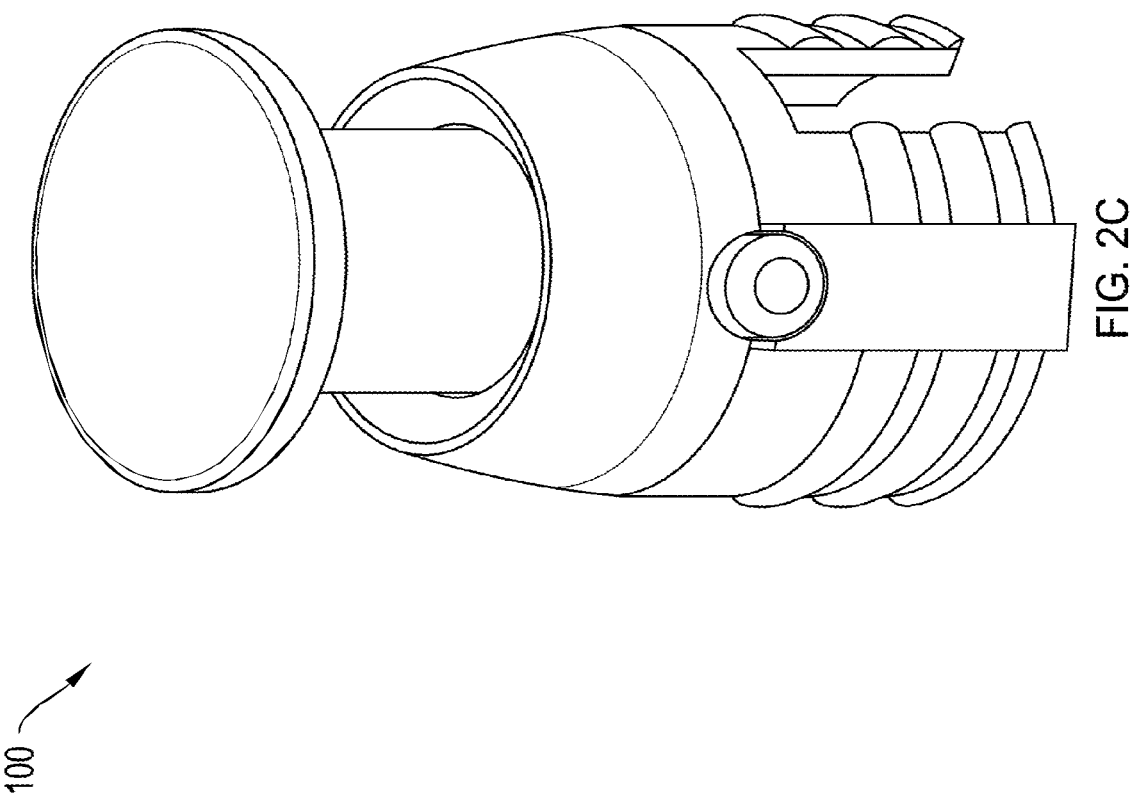
Figure 3:
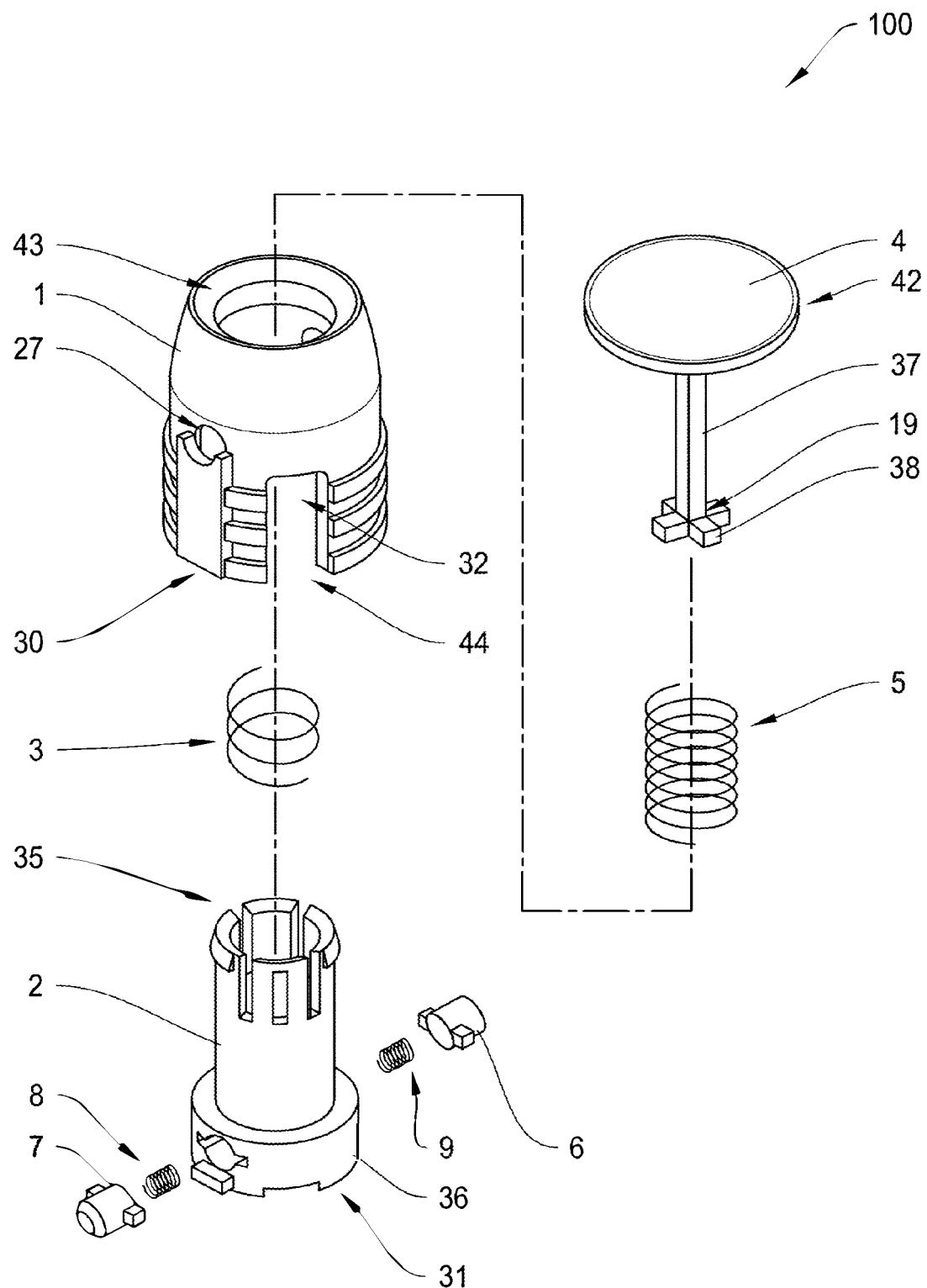

FIGS. 1-2 illustrate a variety of views of one exemplary embodiment of the needle injection device 100. FIGS. 1 and 2 depict device 100 with the drive plunger 2 in a retracted state. FIG. 3 depicts an exploded view of device 100. As seen in FIGS. 1A-2C and 3, device 100 comprises a housing 1 with an inner plunger 4 and drive plunger 2. The drive plunger 2 is associated with a drive spring 3 that provides the force for advancing the drive plunger 2 and needle into the skin of a subject, such as a patient.

The housing 1 comprises a shell with a proximal opening 43 and distal opening 44. The space defined by the shell may receive a drive plunger 2 such that the drive plunger 2 may be in shifting engagement with the housing 1. The drive plunger 2 may move in distal and proximal directions relative to the housing 1. For example, the drive plunger 2 may extend from the proximal opening of the housing in certain positions or from the distal opening of the housing 1 in other positions. In certain embodiments, drive plunger 2 comprises a cylindrical tube with proximal end 35 and distal end 36 and the tube of the drive plunger 2 may define a lumen. The drive plunger 2 may be modified on the proximal end 35 with a handle to allow the user to grasp the handle and extend the drive plunger distally (not shown). The drive plunger 2 may be modified on the distal end 36 with a distal surface 31 dimensioned to receive a needle such as a butterfly needle with infusion tubing attached. The drive plunger 2 may be associated with a drive spring 3, such as a drive spring 3 positioned around the barrel of the drive plunger 2. The drive plunger 2 may be proximally moved by grasping the handle and pulling the proximal end of the drive plunger through the proximal opening of the housing 43 and thereby compressing the drive spring 3.

In certain embodiments, the device further comprises an inner plunger 4 as seen in FIG. 3. The inner plunger 4 may comprise a handle 42, a barrel and a distal end 19. In certain embodiments, when the device comprises an inner plunger 4, the drive plunger 2 is not modified with a handle. The barrel 37 and distal end of the inner plunger 19 may extend through the lumen in the drive plunger 2. The distal end of the drive plunger 36 may define an opening through which the distal end of the inner plunger 19 extends. Protrusions 38 on the distal end of the inner plunger 19 may be dimensioned to lock into the distal end of the drive plunger 36 such that the drive plunger 2 is moved proximally when the inner plunger 4 moves proximally. For example, the distal end of the inner plunger 19 may form a T-shape positioned at the end of the inner injector barrel 38 on the distal end of the drive plunger 36. The T-shape, for example, cannot pass through the opening in the distal end of the drive plunger 36 so the T-shape forces the drive plunger 2 to move proximally when the inner plunger 4 moves proximally.

The drive plunger may be associated with a drive spring 3 such as a spring surrounding the cylinder defining the lumen of the drive plunger 2. The drive plunger 2 may be retracted by pulling the handle 42 of the inner plunger 4 to raise the distal end of the drive plunger 36 into the housing 1. The inner plunger 4 may be manually retracted. For example, the user may hold the housing 1 in one hand and retract the handle 42 of the inner plunger 4 with another hand or with the thumb and forefinger of the hand holding the housing 1. As the drive plunger 2 is retracted, the drive spring 3 associated with the drive plunger 2 is compressed. The drive plunger 2 may be held in a retracted position with one or more stops such as trigger buttons, projections, or locks, e.g., trigger buttons 6 and 7. The one or more stops may extend through windows in the surface of the housing, e.g., windows 27 and 28, and may prevent the spring from releasing and forcing the drive plunger distally (window 28 not shown).

The exterior surface of the cylindrical drive plunger 2 may be modified with one or more stops, e.g., trigger buttons 6 and 7, such that when the drive plunger 2 is retracted as in FIGS. 1 and 2, trigger buttons 6 and 7, which may be spring loaded, each protrude from the housing 1, e.g., trigger button 6 protrudes from a window 27 in the housing 1. When the drive plunger 2 is not retracted, the trigger buttons 6 and 7 may be concealed within the housing 1 between the interior surface of the housing 1 and the exterior surface of the drive plunger 2. In certain embodiments, the drive plunger 2 is modified with two trigger buttons and the buttons may be located in positions on the drive plunger such that the user may contact the two buttons simultaneously. For example, the two trigger buttons 6 and 7 may be located about 90 degrees up to about 180 degrees apart from the other one on the cylindrical body of the drive plunger 2 such that the buttons may be contacted simultaneously with a thumb and forefinger. In certain embodiments, the use of two trigger buttons is preferred to prevent the accidental release of the drive plunger 2 by the compression of one of the buttons. The trigger buttons 6 and 7 may be associated with springs 9 and 8, respectively, which allow each trigger button 6 and 7 to spring out from the window in the housing, e.g. trigger button 6 protrudes from a window 27, when the drive plunger 2 is retracted. The trigger buttons in their extended positions may hold the drive plunger 2 in a retracted position. To release the drive plunger 2, the one or more trigger buttons, e.g., trigger buttons 6 and 7, may be depressed to release the drive plunger 2 and the force of the compressed drive spring 3 forces the drive plunger 2 and needle into the skin of the patient.

Figure 4D:
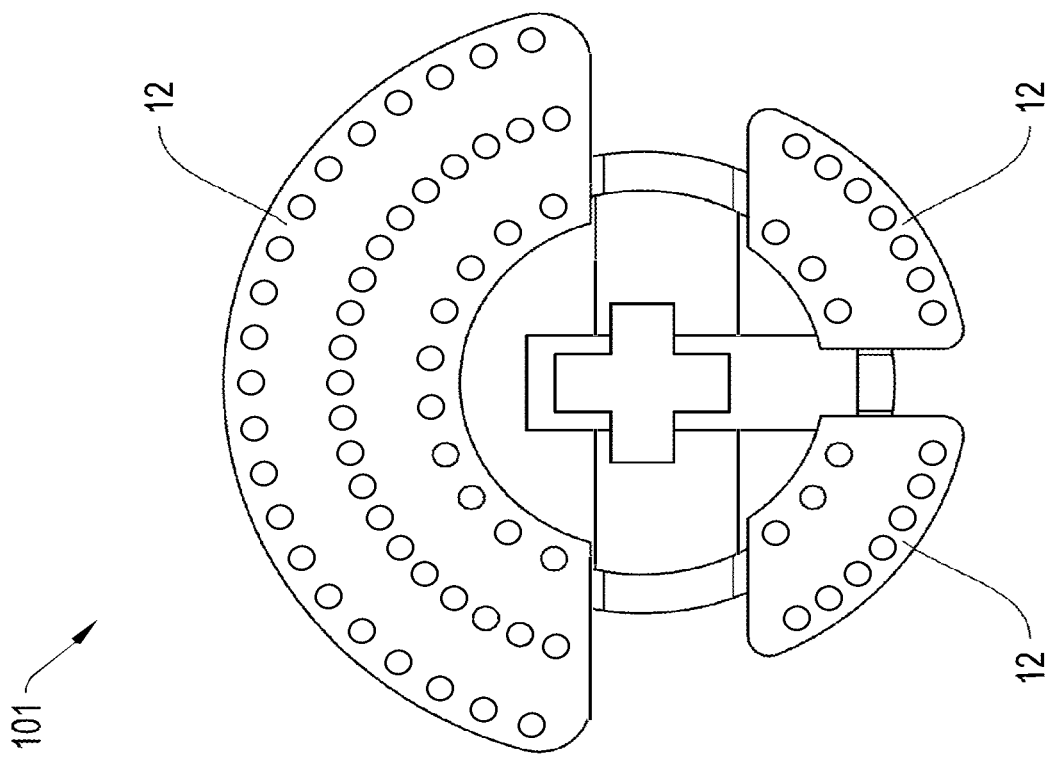
Figure 4C:
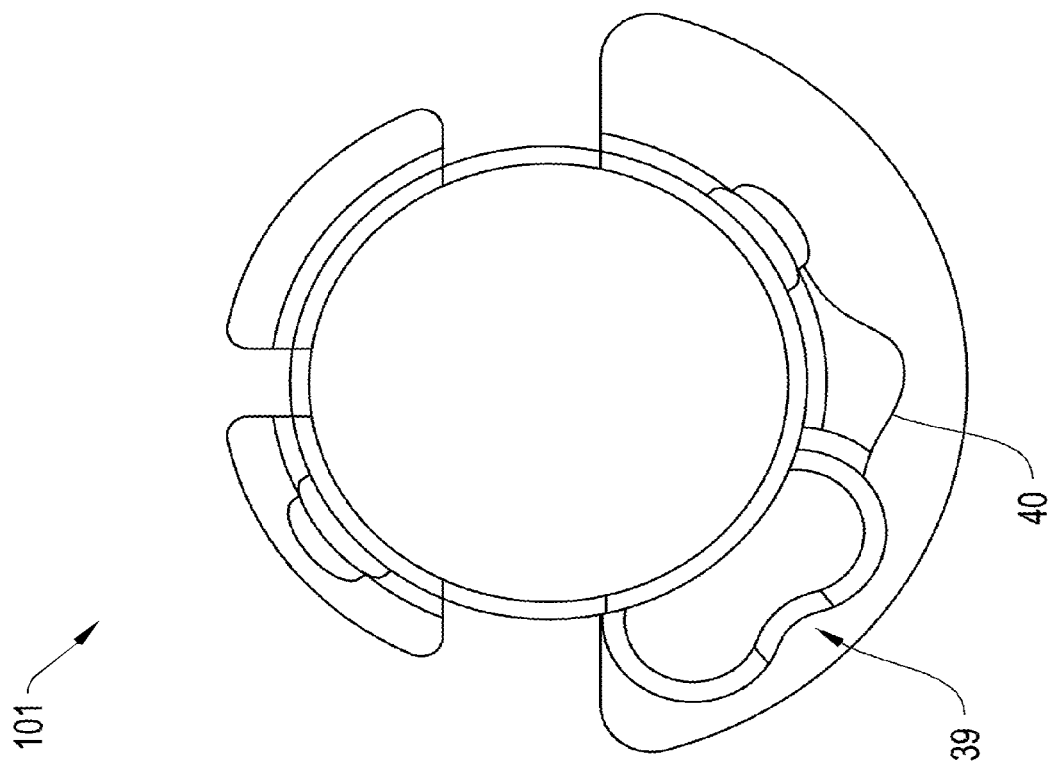
Figure 5C:
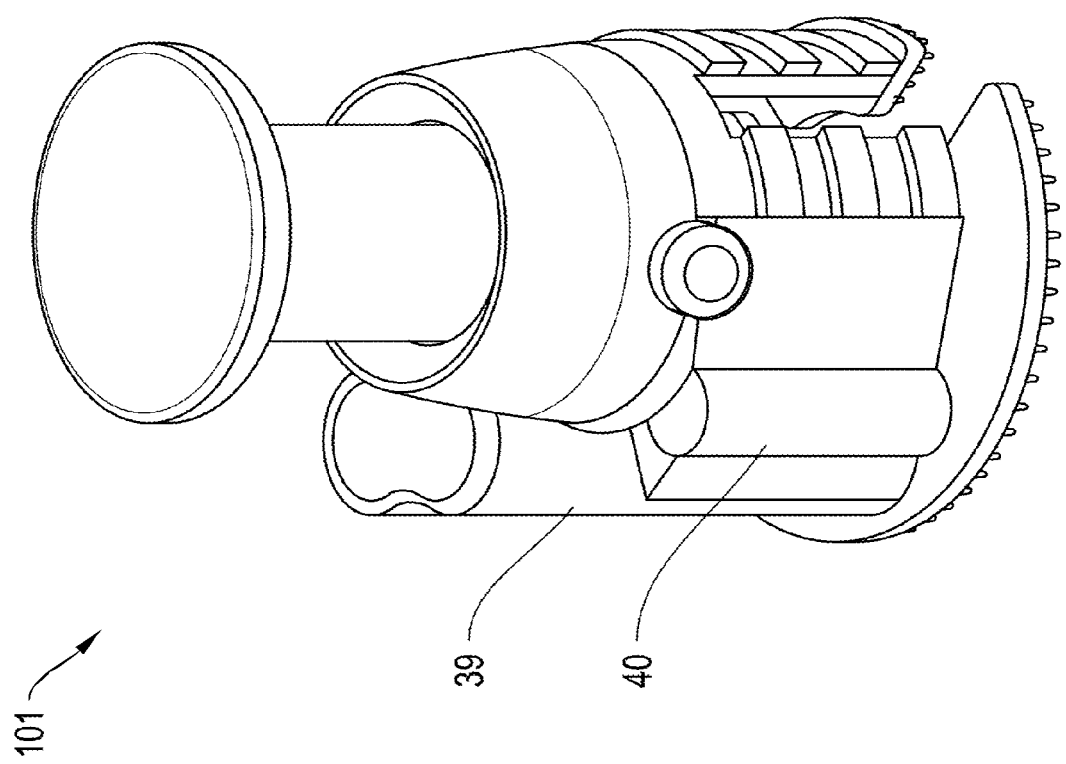
Figure 6:
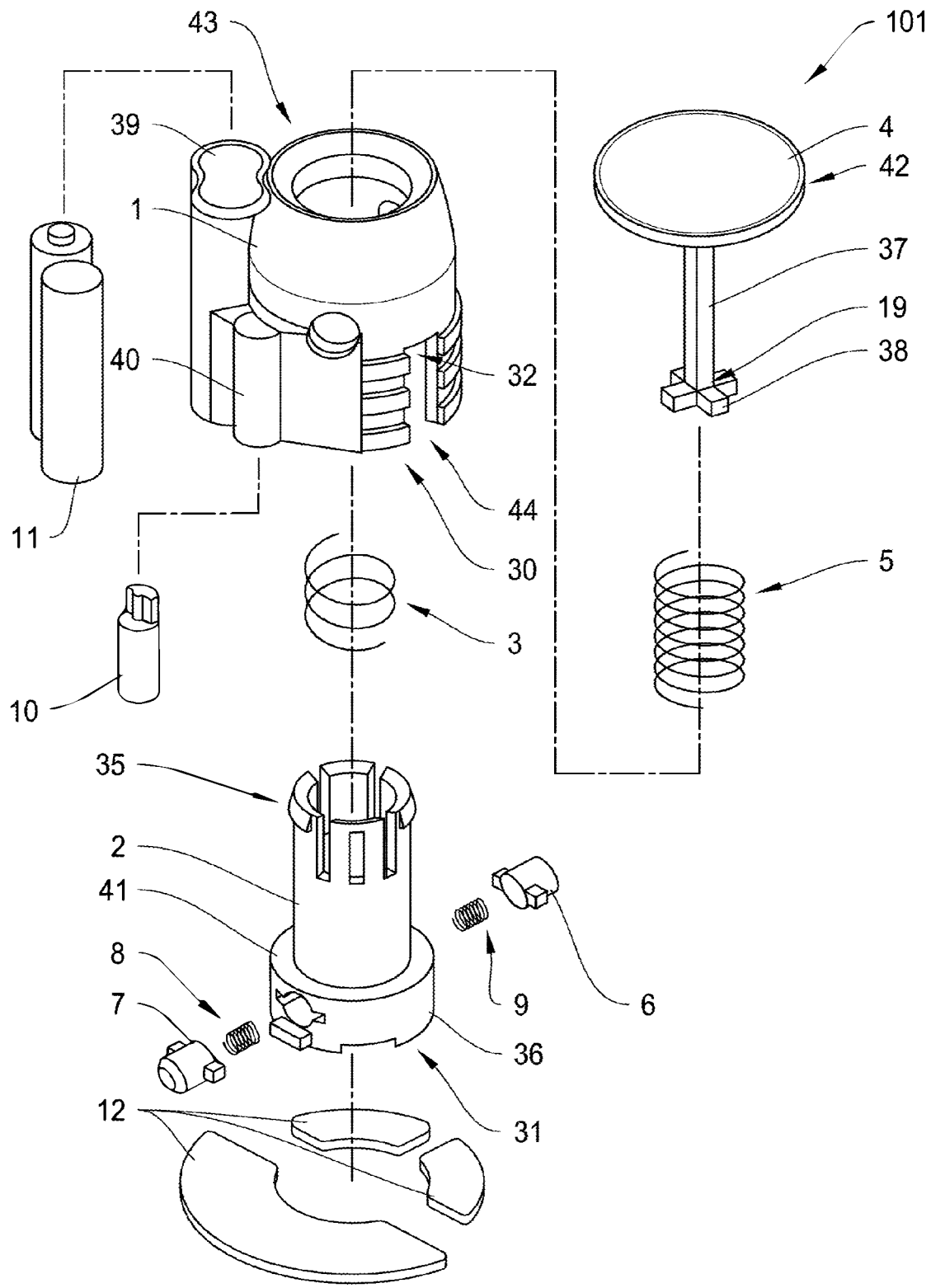

FIGS. 4-5 illustrate a variety of views of an exemplary embodiment of a needle injection device 101. FIG. 6 depicts an exploded view of injection device 101. Distinct from device 100, device 101 comprises textured pads 12 on the distal surface 30 of the housing 1 of the device 101. The distal surface 30 of the housing 1 of the device 101 is the portion of the device 101 that contacts the skin surrounding the site of the injection. FIG. 4D depicts the distal surface 30 of the device with textured pads 12. The distal surface 30 of the housing 1 may be modified with one or more textured pads 12 such as one, two, three or four textured pads 12. The texture on the pads may be in the form of multiple projections on the surface of the pad that extend distally toward the skin of the patient. The projections may extend from 1-3 mm from the surface of the textured pad 12 such as about 1-2 mm from the textured pad 12. The projections may terminate in pointed tips such that skin contact with the textured surface distracts the subject from the pain of needle insertion. In certain embodiments, the textured pads 12 comprise multiple plastic spikes, e.g., needle-like projections or tips, which contact the skin prior and/or during the time of the injection and anesthetize the surface of the skin and/or distract the patient from discomfort associated with the injection. Such projections may be arranged along a perimeter of the distal surface 30 of the housing 1 or in a radial or grid pattern. Projections may be arranged along a portion of the distal surface 30 of the housing or substantially covering the distal surface 30 of the housing 1.

Also distinct from device 100, device 101 comprises a power source 11 and vibrator motor 10. The power source 11 and vibrator motor 10 may be located on the housing, e.g., the power source 11 may be located in a pocket 39 of the housing 1 that envelops the power source 11. The power source 11 may be accessed through a door in the pocket 39 of the housing 1 that permits access into the pocket 39 with the power source 11. In certain embodiments, the power source is a battery and the battery is located in a pocket 39 in the housing 1. The vibrator motor may be located in a pocket 40 in the housing. The vibrator motor 10 may be located in close proximity such as adjacent to the power source 11. In certain embodiments, the vibrator motor 10 is located in proximity to the distal end 44 of the housing 1. In certain embodiments, the power source 11 supplies power to the vibrator motor 10 when the motor is activated.

The vibrator motor 10 may be powered by a power source 11 such as batteries or mechanical means, e.g., a winding mechanism. In certain embodiments, power may be supplied to the vibration motor 10 from the power supply 11, e.g., batteries, upon movement between the housing 1 and drive plunger 2, for example, upon contact with a conductive contact area 41. For example, upon pulling back or setting at least one of the inner and drive plungers in a firing position, electrical contact of a contact area 41 enables a completed circuit thereby starting the vibrator motor 10. In some embodiments, the vibrator motor 10 operates prior to triggering the needle insertion such as several seconds prior to needle insertion to ensure that the active effect of pain lessening is provided.

The vibrator motor 10 may have a speed of between 60 rpm and 15,000 rpm, or in some embodiments, between about 5000 rpm and 10,000 rpm, and in some embodiments, about 9000 rpm. In certain embodiments, the vibrator motor 10 may have a speed of about 6000 rpm to about 10,000 rpm, such as about 7,000 to about 10,000 rpm, such as about 8,000 to about 10,000. The vibrator motor 10 may be structured such that upon motor rotation, a weight is placed on a shaft of the motor or connected to the motor shaft to create an out of balance scenario. Thus, upon motor rotation, oscillations of the out-of-balance shaft may create vibrations.

The vibrator motor 10 may be activated, for example, when the inner plunger 4 is retracted or when the trigger buttons 6 and 7 are depressed. When the vibrator motor 10 is activated, the device 101 vibrates. The vibration of the device in contact with the skin of the subject, distracts the subject from the injection of the needle and/or anesthetizes the skin. In certain embodiments, the device comprises textured pads 12 and a vibration element such as a vibrator motor 10 and power source 11. In other embodiments, the device comprises either the vibration element such as the vibrator motor 10 and power source 11 or the textured pads 12. The device may comprise one or more additional elements for lessening discomfort of needle insertion or distracting the subject from the needle insertion.

Figure 7:
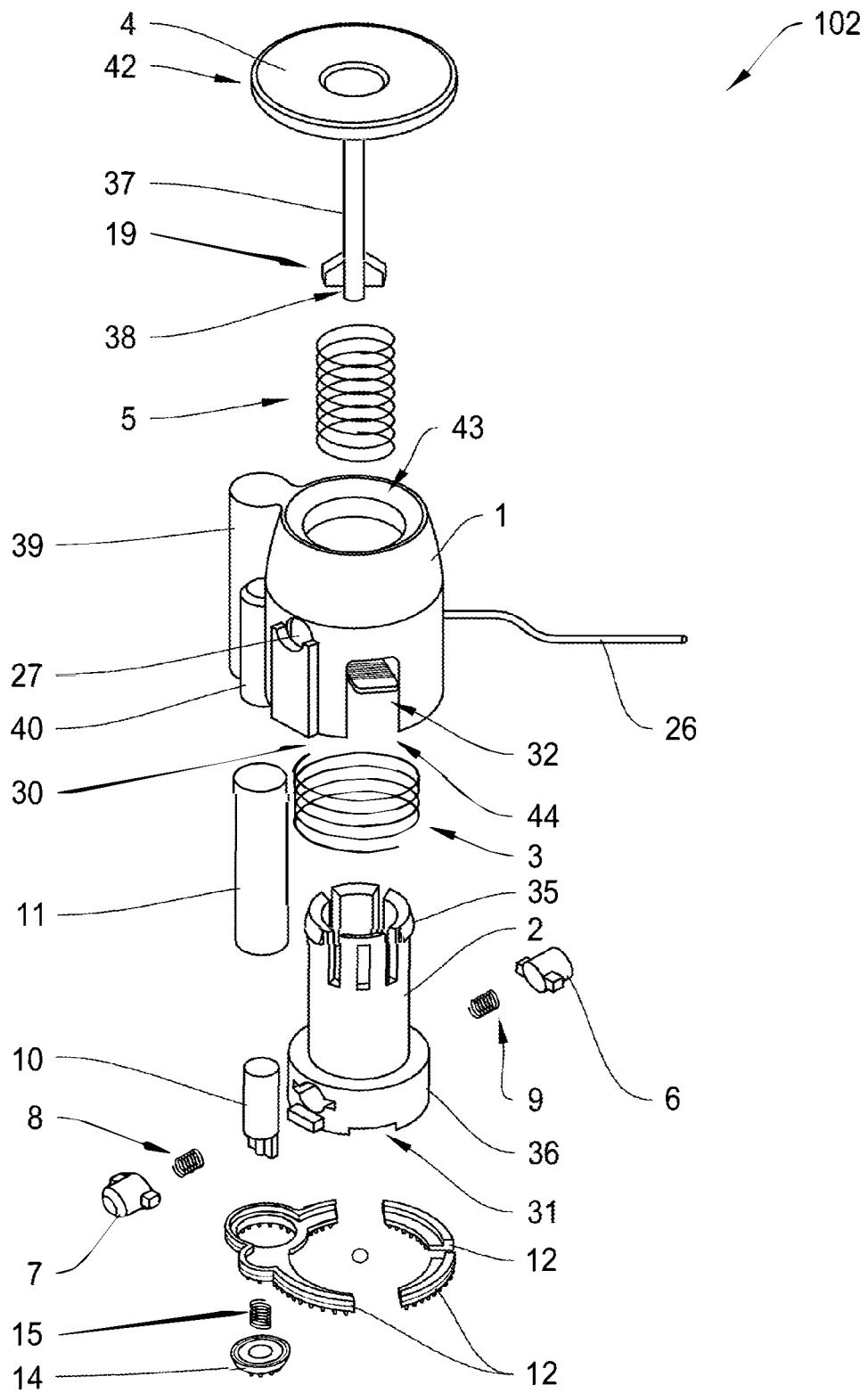

FIG. 7 depicts an exploded view of an exemplary embodiment of a needle injection device 102. Distinct from injection device 101, injection device 102 comprises a contact switch 14 for activating the vibrator motor 10. The contact switch 14, is located on the distal end 44 of the housing 1 and the portion of the contact switch 14 in contact with the skin may be modified with a textured pad such as a pad textured with plastic spikes. When the distal surface 30 of the housing 1 contacts the skin of the patient, the contact switch 14 is depressed and the vibrator motor 10 is activated. The contact switch 14 may be associated with a contact switch spring 15 such that when the contact switch 14 contacts the skin, the contact spring depresses the contact switch spring 15, resulting in the activation of the vibrator motor 10. Once the contact between the skin and the distal end of the housing 1 ceases, the vibrator motor 10 may stop as the spring relaxes to an extended state.

Figure 8:
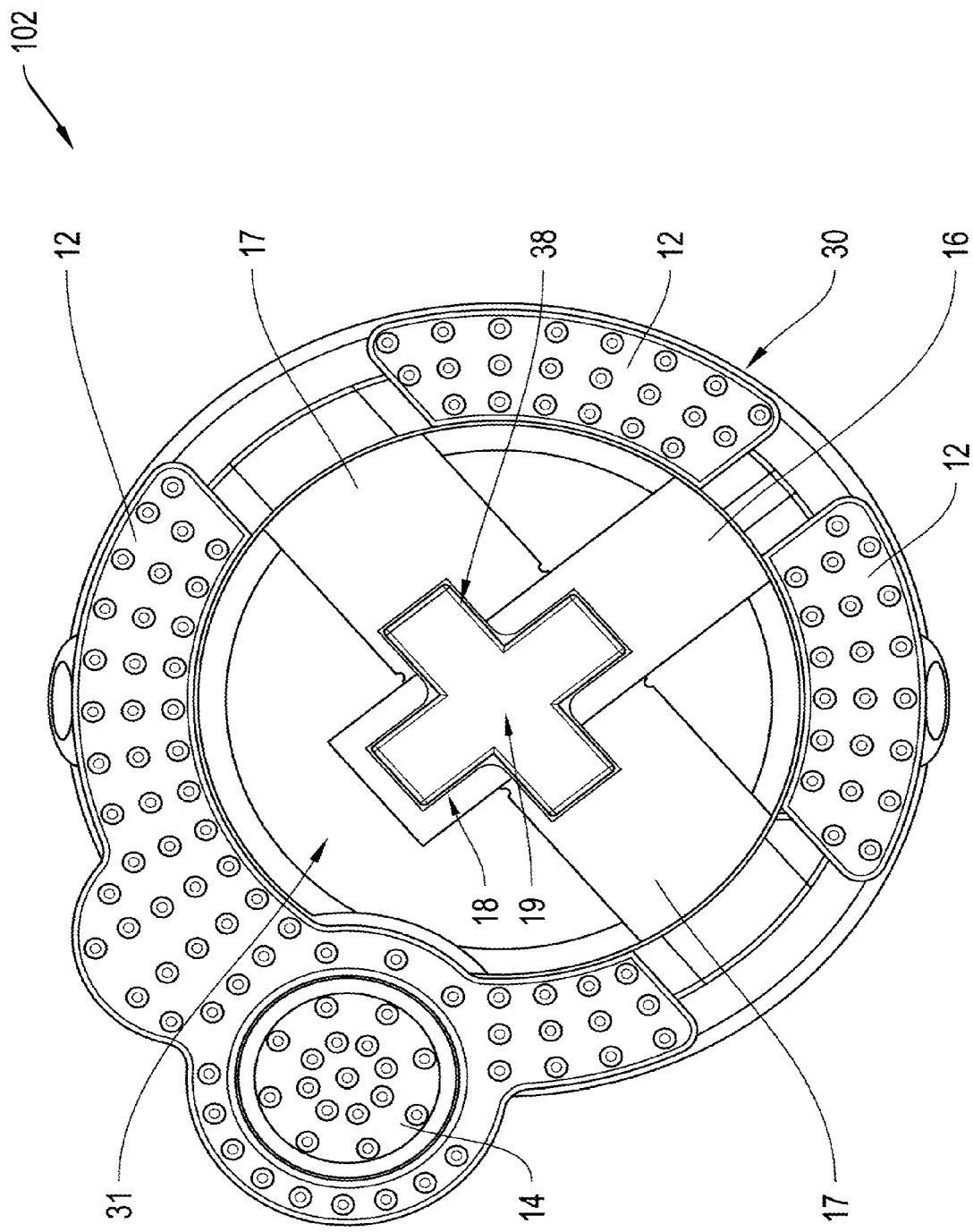

FIG. 8 depicts a bottom view of needle injection device 102. The distal surface 30 of the housing 1 comprises textured pads 12 such as one, two, three or four textured pads 12. The distal surface of the drive plunger 31 comprises recessions 17 and 16 for receiving the wings of a butterfly needle and infusion tubing, respectively. The distal surface of the inner plunger 19 is located in the interior opening 18 of the distal surface of the drive plunger 31. The contact switch 14 may include a textured pad surface.

Figure 9:
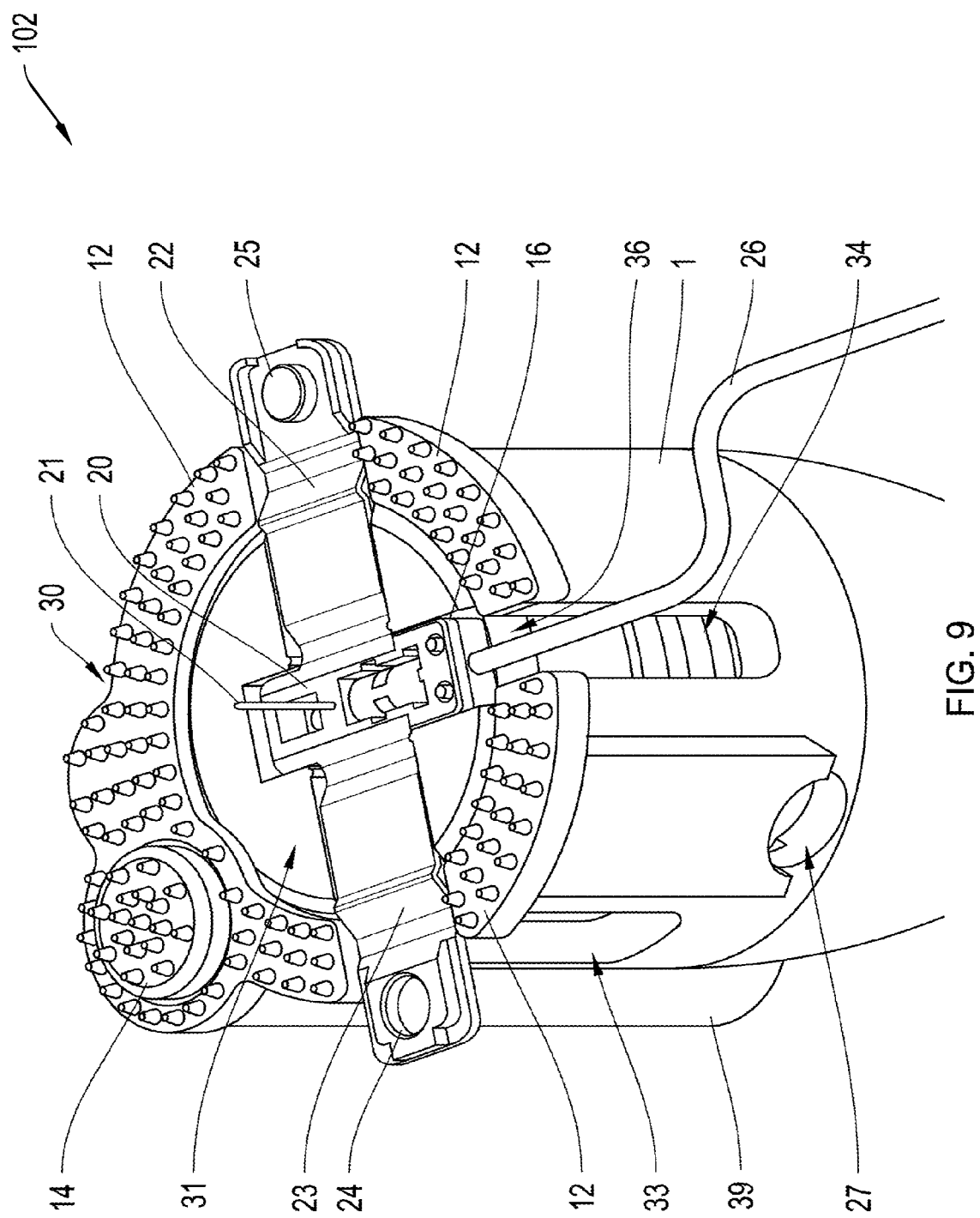
Figure 10:
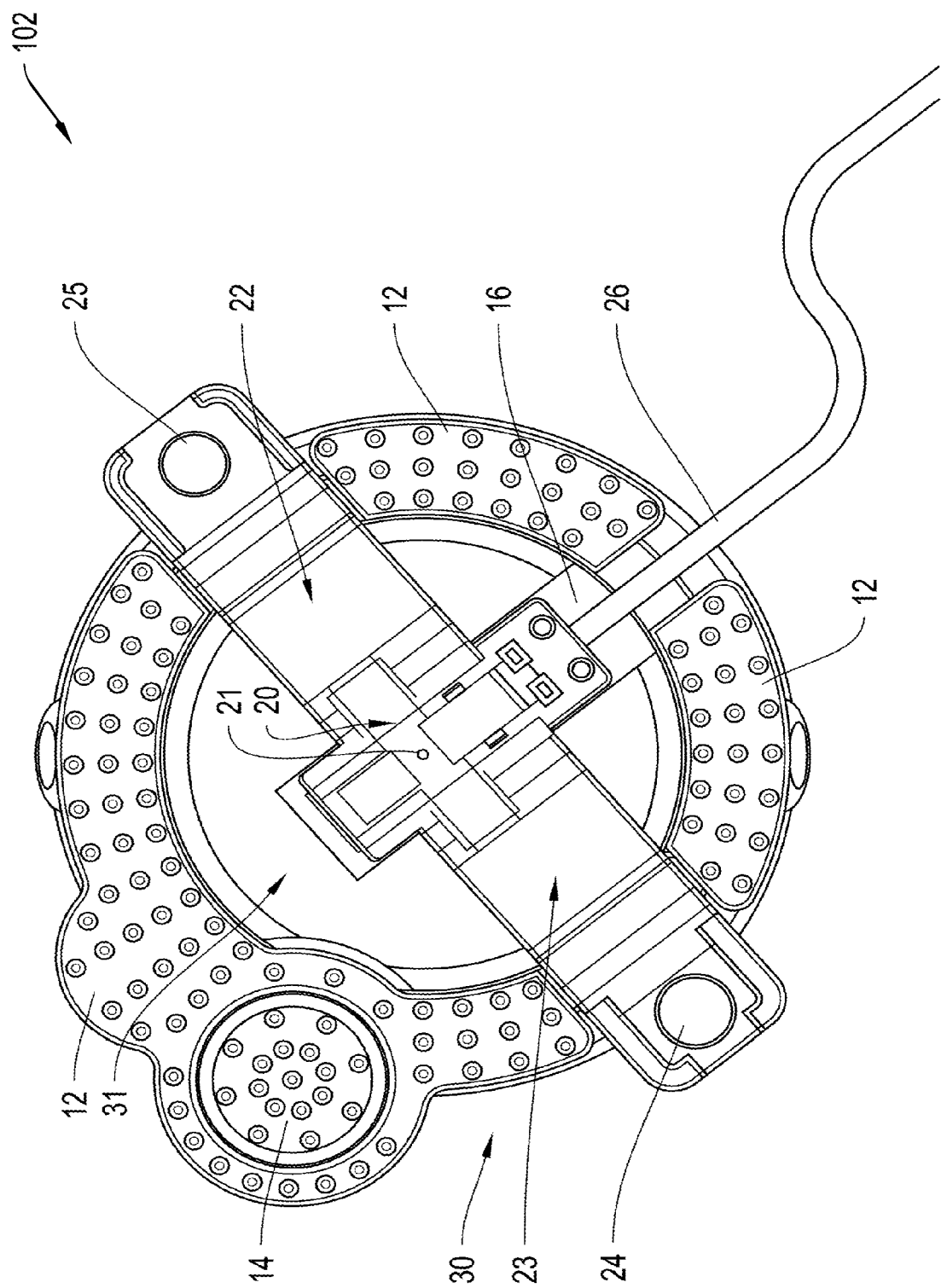

FIG. 9 depicts a perspective bottom view of the needle injection device 102 loaded with a butterfly needle in a non-retracted state. FIG. 10 depicts a bottom view of the needle injection device 102 loaded with a butterfly needle in a non-retracted state. The body of the butterfly needle 20 may be positioned in the center of the distal surface of the drive plunger 31 in contact with the distal surface of the inner plunger 19. The body of the needle extends through recession 16 of the distal surface of the drive plunger 31, while the wings of the butterfly needle are positioned in recessions 17 of the distal surface of the drive plunger 31. Recessions 16 and 17 of the distal surface of the drive plunger 31 may be dimensioned to hold the butterfly needle firmly in place until release is triggered by the compression of the inner plunger 4.

The butterfly needle may be loaded into the distal end of the device by holding the wings together and pushing the body of the butterfly into the recession in the distal surface of the drive plunger 31 dimensioned to receive the body. The wings may be held together through connecting features such as recession 24 and button 25 on opposing wings 22 and 23. The wings 22 and 23 may then be separated and pushed down into recession 17 in the distal surface of the drive plunger 31. Other methods of loading the butterfly needle into the distal surface of the drive plunger include separating the wings 22 and 23 of the butterfly and pressing the wings 22 and 23 into the recessions 17, in the distal surface of the drive plunger 31 thereby forcing the body of the butterfly 20 down into the recession in contact with the distal end of the plunger 19.

In certain embodiments, the needle 21 of the butterfly needle is protected with a sheath such as a plastic sheath. The sheath may be a plastic tube that covers the tip of the needle. The sheath may protect the user from unintentionally piercing skin with the needle, for instance, while opening the butterfly wings or loading the butterfly needle into the device. In certain embodiments, the device may remove the sheath on the needle 21. For example, when the plunger is retracted and the needle is drawn up into the housing of the device, the sheath may be removed during retraction. Removal of the sheath may occur, for example, by an arm on the interior of the housing that extends from the housing toward the needle. When the needle is retracted into the device, the arm may catch the sheath such that the sheath is pulled off of the needle as the needle retracts and the arm remains stationary, for example. The sheath may comprise an arm, a projection, or a disk, for example, which is contacted by the housing during retraction. A component on the interior of the housing such as a detent or projection may contact the arm, projection, or disk of the sheath to remove the sheath during retraction.

FIGS. 9 and 10 depict needle insertion device 102 in a non-retracted loaded state wherein the drive plunger 2 and inner plunger 4 are not retracted and a butterfly needle is loaded into the distal recessions 16 and 17 of the drive plunger 2.

Figure 11:
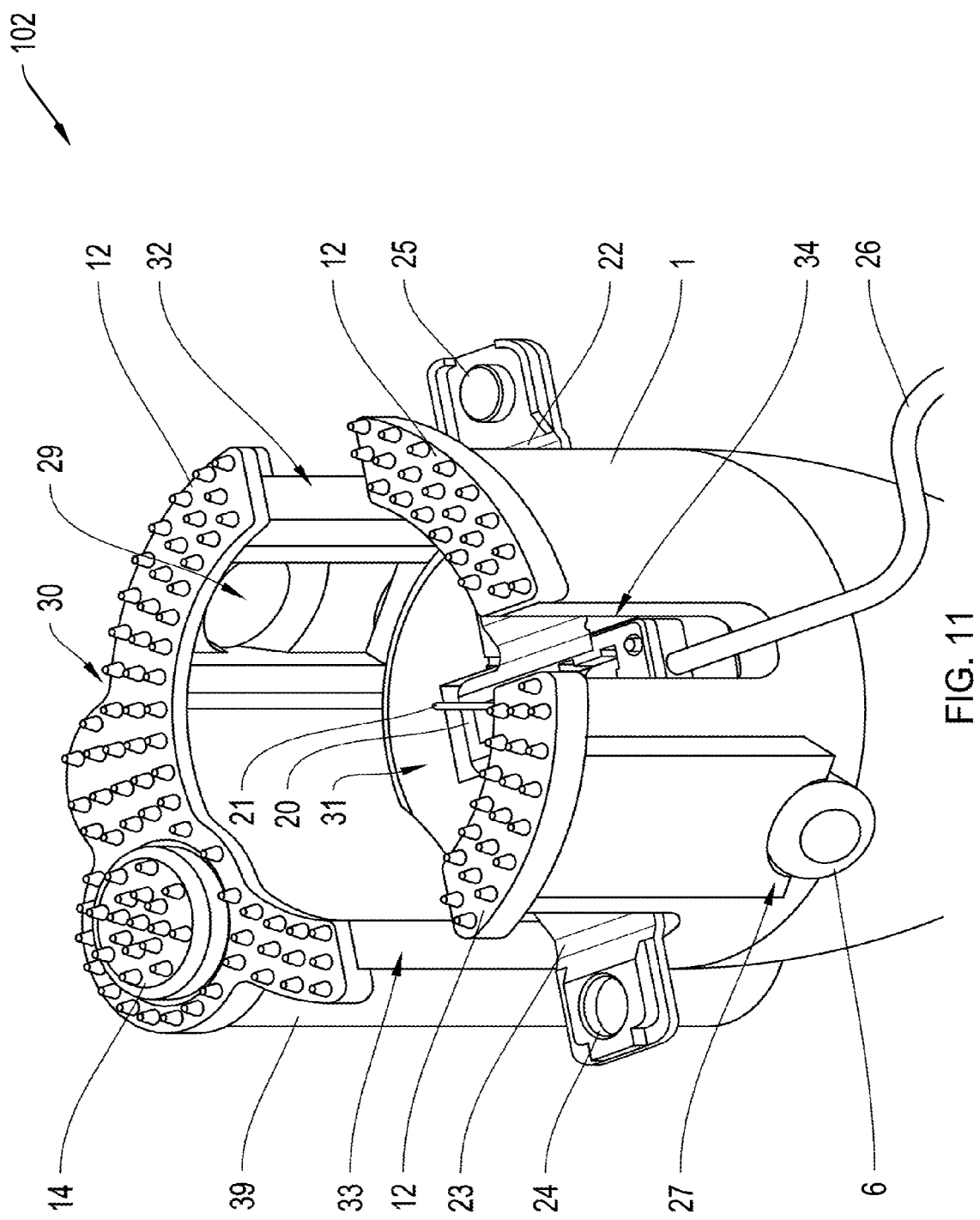
FIG. 11 is a perspective view of the bottom of needle insertion device 102 loaded with a butterfly needle with the drive plunger 2 in a retracted state.
Figure 12:
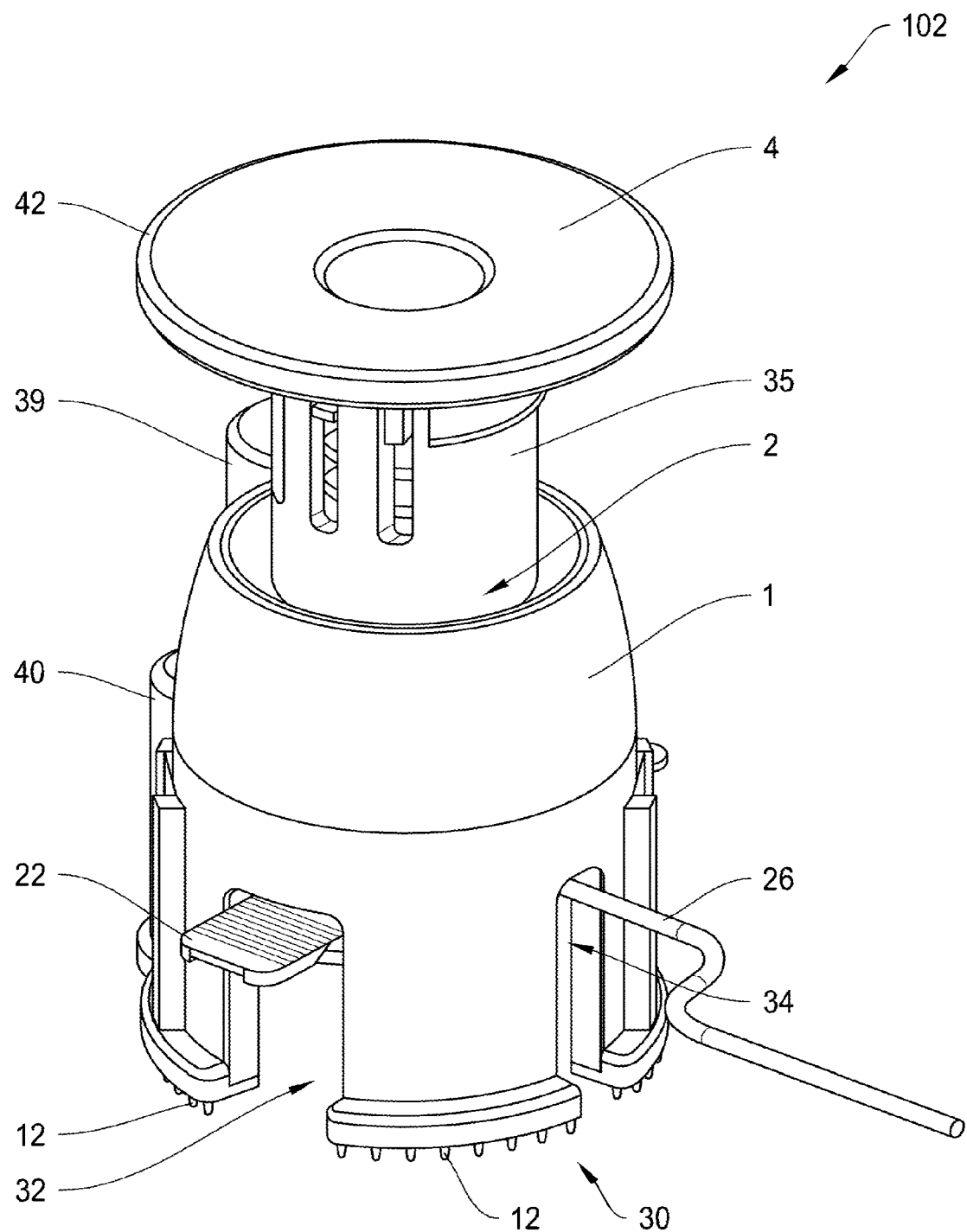
FIG. 12 is a perspective side view of the needle insertion device 102 loaded with a butterfly needle with the drive plunger 2 in a retracted state.

FIGS. 11-12 depict the device 102 in its activated and loaded state. The device is loaded when a needle is positioned in the recessions 16 and 17 in the distal end of the device. To activate the device, the inner plunger 4 may be retracted. To retract the inner plunger 4, the housing 1 may be held in one hand the inner plunger 4 may be pulled in a proximal direction away from the housing 1. The inner plunger 4 and the drive plunger 2 may move together in the proximal direction such that the distal portions of the drive plunger 2 and inner plunger 4 retract together into the interior of the housing when the inner plunger 4 is proximally retracted. As the inner plunger is retracted, the drive spring 3 is compressed.

Trigger buttons 6 and 7, which are concealed inside the housing when the device is not activated, protrude from windows 27 and 28 in the housing of the device in its activated state (window 28 not shown). Trigger buttons 6 and 7 may be attached via springs 9 and 8, respectively, to the exterior of the body of drive plunger 2. In the non-activated state when the plunger is not retracted, a trigger button may rest in a recession in the interior surface of the housing. For example, in FIG. 11, recession 29 may receive trigger button 7 in the non-activated state. The protrusion of trigger button 7 into the recession 29 may help prevent the plunger from retracting into the housing when the needle is being loaded into the device in its non-retracted state. A corresponding recession in the interior of the housing may be present to receive trigger button 6 when the device is in its non-activated state. The contact between the one or more trigger buttons and the one or more recessions on the interior surface of the housing may provide resistance against proximal movement of the drive plunger 2.

When the plunger is retracted to the point where the trigger buttons 6 and 7 may protrude from windows 27 and 28, the trigger buttons extend out through windows 27 and 28 and the plunger is held in a retracted position by the protrusion of the buttons from the housing 1. In the retracted or activated state, the wings of a butterfly needle 22 and 23 extend outside the housing through channels 32 and 33 in the housing 1. The tubing 26 attached to the butterfly needle may extend out through channel 34 of the housing 1 of the device.

As described herein, the device may include various indents, recesses and corresponding projections, one or more pins, one or more prongs, and the like, for forming a stop, setting point, or firing position. Such projections may also be flexible so that they can easily be moved, by for example design, e.g., a wedge, a slide, etc., to go into a recess and/or come out of such recess to effect one or more functions of the device. In some embodiments, the portions are formed as wedge-like members, and/or the like, which are received by corresponding recesses.

For example, in some embodiments, upon pulling back on the inner plunger to move at least one of the inner plunger/ejector and drive plunger into a firing position, certain portions of the inner plunger and/or drive plunger modified with one or more projections are flexed in a first direction so that the projections move into a recess. In some embodiments, the one or more trigger buttons can then be arranged to move the projections out of the recess in, for example, by flexing the projection in a second direction, so that the spring force is released to drive at least one of the inner plunger and drive plunger in a direction for injecting a needle into tissue, and thereby drive the needle into tissue.

In its activated state, the device may be positioned at a location on the patient's body intended for needle injection. For example, the device may be positioned on a section of the abdomen or the thigh. The device may be positioned substantially perpendicularly to the surface of the skin. In certain embodiments, the distal surface 30 of the housing 1 is positioned such that all or a substantial portion of the distal surface 30 of the housing 1 contacts the surface of the skin. For example, each of the textured pads or a substantial portion of one or more textured pads on the distal surface 30 of the housing 1 contact with the surface of the skin. The device may be pressed against the surface of the skin. In certain embodiments, the device is pressed against the surface of the skin such that a contact switch 14 is depressed and a vibrator motor is activated.

In certain embodiments, the pain relieving component may be active for a period of time prior to the injection of the needle. For example, a device with textured pads may be pressed against the skin for a period of about 30 seconds or less, such as about 20 seconds or less, such as about 10 seconds or less preceding the injection of a needle. In other embodiments, a device with a vibrator motor may vibrate in contact with the skin for a period of about 30 seconds or less, such as about 20 seconds or less, such as about 10 seconds or less preceding the injection of a needle. In certain embodiments, a device with both a vibrator motor and one or more textured pads may be active for a period of about 30 seconds or less, such as about 20 seconds or less, such as about 10 seconds or less preceding the injection of a needle.

As the device is pressed against the surface of the skin at the desired location of injection, the trigger button or buttons may be depressed by the user. When the trigger buttons are depressed, the drive spring 3 is released from its compressed state and the drive plunger together with the inner plunger may be released to travel in the distal direction. The tension on the drive spring forces the drive plunger and inner plunger to accelerate rapidly in the distal direction and the drive the needle into the skin of the patient.

In certain embodiments, the depression of the trigger buttons drives the needle into the skin of the patient and releases the needle from the device. In other embodiments, the needle is not released from recessions 16 and 17 in the distal surface of the drive plunger 31 following depression of the trigger buttons and an extra step is required to release the needle body 20 from the device. In certain embodiments, once the drive plunger 2 has been released and the needle is positioned in the tissue of the patient, the body of the needle 20 is released from the device by depressing the inner plunger 4. The inner plunger 4 is associated with an ejector spring 5 that compresses when the inner plunger 4 is depressed and releases the needle from the device. Once the user stops depressing the inner plunger 4, the plunger springs back to an extended position.

In certain embodiments, the distal end of the inner plunger 19 comprises protrusions 38 extending from the distal side of the opening in the distal end of the drive plunger 19. The protrusions 38 may allow the inner plunger to grab the distal surface of the drive plunger when the inner plunger 4 is retracted such that when the inner plunger 4 is retracted, the drive plunger 2 is concurrently retracted. In the distal direction, the inner plunger 4 may slide independently in the lumen of the drive plunger to eject the needle from recessions 16 and 17 in the distal end of the drive plunger 31 by contacting the body of the needle and forcing the needle in the distal direction.

In certain embodiments, the inner plunger 4 is associated with an ejector spring 5. When the inner plunger 4 is depressed on the device in a non-retracted state in the distal direction, the inner plunger 4 compresses the ejector spring 5. The inner plunger 4 travels in the distal direction such that the protrusions 38 on the distal end of the inner plunger 19 extend distally from the distal surface of the drive plunger 36. As the inner plunger 4 is depressed distally, the body of the butterfly needle is pushed out from recessions 16 and 17 in the distal surface of the drive plunger 31 disconnecting the needle from the device. When the user stops depressing the head of the inner plunger, the compression created on the ejector spring 5 forces the head of the inner plunger 4 up to a rested position.

The invention provides methods for administering a needle to a subject such as a patient in need thereof. A user of the device may load the device such as any one of devices described herein, e.g., 101, 102 or 103, with a needle such as a butterfly needle. The needle may be loaded into the device by pressing the needle into the recessions in the distal surface of the drive plunger. Once the device is loaded, the user may retract the plunger to the point in which the plunger is stopped and held in a retracted position, for example, by the trigger buttons. The user may then position the device on the surface of the skin such that the distal surface of the housing contacts the skin. For certain embodiments, the user may press the distal surface of the housing against the skin to trigger a distracting or anesthetizing effect of the textured pads and/or to activate the contact switch of the vibrator motor. The pain relieving component may be active for a period of time preceding the injection of the needle, such as about 30 seconds or less, about 20 seconds or less or about 10 seconds or less. The user may then release the plunger, for example, by depressing the trigger button or buttons. In certain embodiments, the plunger may be depressed to release the needle from the recessions in the drive plunger. In certain embodiments, the user may secure the needle to the surface of the skin with an adhesive such as tape. The invention further provides methods for relieving the pain of needle injections. In certain embodiments, the invention provides a device for relieving pain comprising a pain relieving component such as a textured pad and/or a vibrating elements. The device may comprise a housing with a contact switch on the distal surface such that contacting the distal surface of the device to the skin relieves pain such as the pain of needle injections. In certain embodiments, the device for relieving pain does not also inject a needle.

Embodiments of the present disclosure may be used, for example, for needle stick tests for diabetics, intravenous catheter insertion, subcutaneous catheter insertion, blood sampling, superficial surgical procedures, and topical anesthesia of leg ulcers for cleansing or debridement. Also, some embodiments can be used to numb the skin for tattooing as well as electrolysis and laser hair removal.

Although a few variations have been described in detail above, other modifications are possible. For example, any logic flow depicted in the accompanying figures and described herein does not require the particular order shown, or sequential order, to achieve desirable results. Other implementations may be within the scope of at least some of the following exemplary claims.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents.

What is claimed:

1. A device for administering a butterfly needle to a subject, comprising:
   a housing comprising a shell with a distal opening and a proximal opening, with two opposing grooves extending from the distal opening towards the proximal opening, a distal surface disposed at least partially about the distal opening;
   a drive plunger occupying the space defined by the shell of the housing and in shifting engagement with the housing, wherein the drive plunger has a proximal end with a handle extending from the proximal opening of the housing and a distal end dimensioned to receive and deliver the butterfly needle, the distal end further including depressions aligned to the two opposing grooves of the housing to permit a butterfly needle having wings to be received with each wing extending beyond the housing;
   a drive spring associated with the drive plunger such that when the handle is retracted proximally relative to the housing, the drive spring compresses and when the drive plunger is released, the drive plunger travels distally from the force of the drive spring;
   a stop to hold the drive spring in a retracted position; and
   a component for relieving discomfort associated with injecting the butterfly needle to the subject receiving the injection.

2. The device of claim 1, further including an inner plunger occupying a lumen of the drive plunger and comprising a handle extending from the proximal opening of the housing and in connection with the proximal end of the drive plunger, a barrel and a distal end in proximal shifting engagement with the drive plunger such that when the handle of the inner plunger is retracted proximally relative to the housing, the drive plunger is retracted, wherein the drive spring is associated with the drive plunger such that when the handle of the inner plunger is retracted proximally relative to the housing, the drive spring compresses and when the drive plunger is released, the drive plunger travels distally from the force of the drive spring.

3. The device of claim 1, wherein the component for relieving discomfort further comprises a vibrator motor and power source associated with the housing such that the power source supplies power to the vibrator motor when the motor is activated.

4. The device of claim 2, wherein the component for relieving discomfort further includes a textured pad on the distal surface of the housing.

5. The device of claim 1, wherein the stop is a button extending from the surface of the drive plunger, depression of the button releasing the drive plunger from its retracted state.

6. The device of claim 1, wherein when the drive plunger is released, the butterfly needle is injected into the skin of the subject.

7. The device of claim 6, wherein when the butterfly needle is injected into the skin of the subject, the distal end of the drive plunger releases the needle from the device.

8. The device of claim 1, wherein the butterfly needle is attached to infusion tubing, the housing further comprising a tubing channel extending from the distal opening towards the proximal opening, the infusion tubing attached to the butterfly needle extending through the tubing channel.

9. The device of claim 1, wherein the distal surface of the housing is divided into at least 2 distinct parts with the two opposing grooves of the housing therebetween.

10. A device for administering a butterfly needle having wings to a subject, comprising:
    a housing comprising a shell with a distal opening and a proximal opening, with two opposing grooves extending from the distal opening towards the proximal opening, a distal surface disposed at least partially about the distal opening;
    a drive plunger occupying the space defined by the shell of the housing and in shifting engagement with the housing, wherein the drive plunger has a proximal end with a handle extending from the proximal opening of the housing and a distal end dimensioned to receive and deliver the butterfly needle, the distal end further including holders for receiving the wings of the butterfly needle, the holders aligned to the two opposing grooves of the housing to permit each wing of the butterfly needle to extend from the housing;

a drive spring associated with the drive plunger such that when the handle is retracted proximally relative to the housing, the drive spring compresses and when the drive plunger is released, the drive plunger travels distally from the force of the drive spring;

a stop to hold the drive spring in a retracted position; and a component for relieving discomfort associated with injecting the butterfly needle to the subject receiving the injection.

11. The device of claim 10, further including an inner plunger occupying a lumen of the drive plunger and comprising a handle extending from the proximal opening of the housing and in connection with the proximal end of the drive plunger, a barrel and a distal end in proximal shifting engagement with the drive plunger such that when the handle of the inner plunger is retracted proximally relative to the housing, the drive plunger is retracted, wherein the drive spring is associated with the drive plunger such that when the handle of the inner plunger is retracted proximally relative to the housing, the drive spring compresses and when the drive plunger is released, the drive plunger travels distally from the force of the drive spring.

12. The device of claim 10, wherein the holders in the distal end of the drive plunger are dimensioned to hold the butterfly needle firmly in place.

13. The device of claim 10, wherein the component for relieving the discomfort to the patient is selected from one or more of: a textured pad on the distal surface of the housing and a vibrator component comprising a vibrator motor and power source associated with the housing such that the power source supplies power to the vibrator motor when the motor is activated.

14. The device of claim 10, wherein when the drive plunger is released, the butterfly needle is injected into the skin of the subject.

15. The device of claim 14, wherein when the butterfly needle is injected into the skin of the subject, the distal end of the drive plunger releases the needle from the device.

16. The device of claim 10, wherein the butterfly needle is attached to infusion tubing, the housing further comprising a tubing channel extending from the distal opening towards the proximal opening, the infusion tubing attached to the butterfly needle extending through the tubing channel.

17. The device of claim 10, wherein the distal surface of the housing is divided into at least 2 distinct parts with the two opposing grooves of the housing therebetween.

18. A device for administering a butterfly needle to a subject, comprising:

a housing comprising a shell with a distal opening and a proximal opening, with two opposing apertures extending from the distal opening towards the proximate opening, a distal surface disposed at least partially about the distal opening;

a drive plunger occupying the space defined by the shell of the housing and in shifting engagement with the housing, wherein the drive plunger has a proximal end with a handle extending from the proximal opening of the housing and a distal end dimensioned to receive and deliver the butterfly needle, the distal end further including receivers aligned to the two opposing apertures of the housing to permit a butterfly needle having wings to be received with each wing extending beyond the housing;

a drive spring associated with the drive plunger such that when the handle is retracted proximally relative to the housing, the drive spring compresses and when the drive plunger is released, the drive plunger travels distally from the force of the drive spring;

a stop to hold the drive spring in a retracted position; and a component for relieving discomfort associated with injecting the butterfly needle to the subject receiving the injection.

19. The device of claim 18, further including an inner plunger occupying a lumen of the drive plunger and comprising a handle extending from the proximal opening of the housing and in connection with the proximal end of the drive plunger, a barrel and a distal end in proximal shifting engagement with the drive plunger such that when the handle of the inner plunger is retracted proximally relative to the housing, the drive plunger is retracted, wherein the drive spring is associated with the drive plunger such that when the handle of the inner plunger is retracted proximally relative to the housing, the drive spring compresses and when the drive plunger is released, the drive plunger travels distally from the force of the drive spring.

* * * * *